(12) United States Patent
Abo et al.

(10) Patent No.: US 7,442,534 B2
(45) Date of Patent: Oct. 28, 2008

(54) NUCLEIC ACIDS AND POLYPEPTIDES WHICH RESEMBLE RHO AND WHICH INTERACT WITH CELL SIGNALLING PATHWAYS AND PROTEINS

(75) Inventors: Arie Abo, Oakland, CA (US); Ami Aronheim, Binyamina (IL)

(73) Assignee: Onyx Pharmaceuticals, Inc., Emeryville, CA (US)

( * ) Notice: Subject to any disclaimer, the term of this patent is extended or adjusted under 35 U.S.C. 154(b) by 988 days.

(21) Appl. No.: 10/330,372

(22) Filed: Dec. 27, 2002

(65) Prior Publication Data

US 2003/0119146 A1 Jun. 26, 2003

(51) Int. Cl.
*C12N 9/14* (2006.01)
*C07K 14/47* (2006.01)

(52) U.S. Cl. .............................. 435/195; 530/350

(58) Field of Classification Search ................ 435/194; 530/324, 326, 350
See application file for complete search history.

(56) References Cited

U.S. PATENT DOCUMENTS 6,500,653 B1 12/2002 Abo et al. .................. 435/194

FOREIGN PATENT DOCUMENTS

WO    WO 96 20948    7/1996

OTHER PUBLICATIONS

SIGMA Catalog (1997, p. 1159, product G5149).*
Mary Ann Sells and Jonathan Chernoff, "Emerging from the Pak: the p21-activated protein kinase family," Trends in Cell Biology, vol. 7, Issue 4, Apr. 1997, pp. 162-167.
Martin, A.G., et al., "A novel serine kinase activated by rac1/CDC42Hs-dependent autophosphorylation is related to PAK65 and STE20," EMBO, vol. 14, No. 9, 1995, pp. 1970-1978.
Aronheim et al. "Chp, a homologue of the GTPase Cdc42Hs, activates the JNK . . . " Current Biology (1998), vol. 8, No. 20, pp. 1125-1128.
Nucleotide Sequence Database EMBL, ID: HSZZ3005; Acc. No. AA367838, Apr. 1997, Adams et al.
Bagrodia et al. "Cdc42 and PAK-mediated Signaling Leads to Jun Kinase and p38 Mitogen-activiated Protein Kinase Activation" (1995), Jnl. Biol. Chem. vol. 270, No. 47, pp. 27995-27998.
Nobes et al. "Rho, Rac, and Cdc42 GTPases Regulate the Assembly . . . " (1995) Cell, vol. 81, pp. 53-62.
Aromheim et al. (Jun. 1997) Molecular and Cellular Biology, vol. 17. pp. 3094-3102.
NCBI Genbank Accession No. AAL17966, Rho family GTPase Chp [Homo sapiens], Feb. 13, 2002.
NCBI Genbank Accession No. AAH86990, Ras homolog gene family, member V [Rattus norvegicus], Jul. 25, 2005.
Erickson, J.W., et al., "Mammalian Cdc42 is a brefeldin A-sensitive component of the Golgi apparatus," J Biol Chem. Oct. 25, 1996;271(43):26850-4.

* cited by examiner

*Primary Examiner*—Elizabeth Slobodyansky
(74) *Attorney, Agent, or Firm*—Gary R. Fabian; Gregory J. Giotta

(57) ABSTRACT

The present invention relates to an isolated full-length Chp polypeptide, a biologically-active polypeptide fragment thereof, and nucleic acids which code for it. This polypeptide has various activities in regulating cell signaling and signal transduction pathways, including, e.g., a PAK regulatory domain binding activity, a PAK kinase stimulatory activity, a JNK kinase stimulatory activity, a cytoskeletal-reorganizing activity, or a Chp-specific immunogenic activity. The invention relates to all aspects of Chp, or homologs thereof, including assays for modulators, activators, ligands, etc.

14 Claims, 2 Drawing Sheets

```
GGAATTCGGCACGAGAGATTGTCAGCGTCCGGCTGCGGAACCTGCCTCCCTGAGCGCCGAGCTGGTCCGGCTGCCCCTCTGCTACC  90
CCGGGAGCGGCCATGCCGCCGCGGGAGCTGAGCGAGGCCGAGCCTCCGACCCTCGACCCCTGAGCCGCCTCCGCGGCCAGCGCC  180
           M  P  P  R  E  L  S  E  A  E  P  P  L  P  A  S  T  P  P  R  R  R  S  A
CCTCCGGAGCTGGGCATCAAATGCGTGCTGGTGGGCGATGGCGCGGTGGGCAAGAGCAGCCTCATCGTCAGCTACACCTGCAATGGATAC  270
  P  P  E  L  G  I  K  C  V  L  V  G  D  G  A  V  G  K  S  S  L  I  V  S  Y  T  C  N  G  Y
CCCTCCGCGCTATCGGCCTACAGCACTTTCTCCGTGCAAGTCCTGGTAGATGGAGCCCCTGTGCGAGTCTTCAGCTTGGGACACA  360
  P  S  R  Y  R  P  T  A  L  D  T  F  S  V  Q  V  L  V  D  G  A  P  V  R  I  E  L  W  D  T
GCAGGGCAGGAGGACTTTGACCGGCTTCGTTCTCTGAGATACCGATGTCTTTCTGCTTCAGCGTGGTCAGCCCAGC  450
  A  G  Q  E  D  F  D  R  L  R  S  L  C  Y  P  D  T  D  V  F  L  A  C  F  S  V  V  Q  P  S
TCCTTTCAAAACATAACAGAAAAAATGGCTGCCGAGATCCGACCACTCACAACCCCAAGCACCTGTTGCTGGTGGGCACTCAGGCCGAC  540
  S  F  Q  N  I  T  E  K  W  L  P  E  I  R  T  H  N  P  Q  A  P  V  L  L  V  G  T  Q  A  D
CTGAGGGACGATGTCAATGTACTAATTCAGTTGGACCAAGGAGGTCGGGAGGGCAGAGAACTTGACGCAGCTTGTCGACTGTTGCTGAGT  630
  L  R  D  D  V  N  V  L  I  Q  L  D  Q  G  G  R  E  G  P  V  P  E  P  Q  A  Q  G  L  A  E
AAGATCCGGGCCTGCTACCTTGAGTGCTCAGCCTTGACCCAGAAGAACCTGAAGGAGGTGTTCGACTCGGCCATTCTCAGTGCGATT  720
  K  I  R  A  C  Y  L  E  C  S  A  L  T  Q  K  N  L  K  E  V  F  D  S  A  I  L  S  A  I
GAGCACAAAGCCCGCCTGGAGAAGAAACTGAACGCAAAAGGTGTGCGACTCTCTCCGCTGTCGCTGAAGAAGTTCTTCTGCTTTGTT  810
  E  H  K  A  R  L  E  K  K  L  N  A  K  G  V  R  T  L  S  R  C  R  W  K  K  F  F  C  F  V
TGAGCAGCTATGGCAGTGCAAGAGATAGGCAGGTGGCCTGAGACTTCTGAGACATCGGGTACTGGCCAGGCCTGGCCAACCCC  900
TGGGACTCAGTTCTCTATTGAACACAGGGGATATGGCCTCAAAGCTGTACACTCTGGTAAGCCAGGGTGCCTCTGTCCTGTCAAGG  990
GCTGGCTGATTTGGATTTCTTTGGTCAAGACTCACAGGAAATCCCAGCACTTTGGTTTTCATGGGATAGTTCCATCAGTGTCAGTAGCG  1080
CTGAGCAGCTTGTGATGTAATTCTCAGTTTCTTATCCTGGCCACACAGGTCAGTTTGGCTGAATGCCAGGTCCCTCGCTGGGTCCTCACCC  1170
TCTCCTAGCACAGGTGTGACAAAGCTAGGAAGGAAAAACAGTGAGGCATCCTGAGGGCT  1230

FIGURE 1
```

```
Chp     1    M P P R E L S E A E P P P L P A S T P P P R R R S A P P E L
Cdc42   1    M Q T - - - - - - - - - - - - - - - - - - - - - - - - - - - -
Rac1    1    M Q A - - - - - - - - - - - - - - - - - - - - - - - - - - - -

Chp     31   G I K C V L V G D G A V G K S S L I V S Y T C N G Y P S R Y
Cdc42   4    - I K C V V V G D G A V G K T C L L I S Y T T N K F P S E Y
Rac1    4    - I K C V V V G D G A V G K T C L L I S Y T T N A F P G E Y

Chp     61   R P T A L D T F S V Q V L V D G A P V R I E L W D T A G Q E
Cdc42   33   V P T V F D N Y A V T V M I G G E P Y T L G L F D T A G Q E
Rac1    33   I P T V F D N Y S A N V M V D G K P V N L G L W D T A G Q E

Chp     91   D F D R L R S L C Y P D T D V F L A C F S V V Q P S S F Q N
Cdc42   63   D Y D R L R P L S Y P Q T D V F L V C F S V V S P S S F E N
Rac1    63   D Y D R L R P L S Y P Q T D V F L I C F S L V S P A S F E N

Chp     121  I T E K W L P E I R T H N P Q A P V L L V G T Q A D L R D D
Cdc42   93   V K E K W V P E I T H H C P K T P F L L V G T Q I D L R D D
Rac1    93   V R A K W Y P E V R H H C P N T P I I L V G T K L D L R D D

Chp     151  V N V L I Q L D Q G G R E G P V P E P Q A Q G L A E K I R A
Cdc42   123  P S T I E K L A K N - K Q K P I T P E T A E K L A R D L K A
Rac1    123  K D T I E K L K E K - K L T P I T Y P Q G L A M A K E I G A

Chp     181  C C Y L E C S A L T Q K N L K E V F D S A I L S A I E H K A
Cdc42   152  V K Y V E C S A L T Q K G L K N V F D E A I L A A L - E P P
Rac1    152  V K Y L E C S A L T Q R G L K T V F D E A I R A V L C P P P

Chp     211  R L E K K L N A K G V R T L S R C R W K K F F C F V
Cdc42   181  E P K K S - - - - - - - - - R R C V - - - - - - L L
Rac1    182  V K K R K - - - - - - - - - R K C L - - - - - - L L
```

Figure 2

NUCLEIC ACIDS AND POLYPEPTIDES WHICH RESEMBLE RHO AND WHICH INTERACT WITH CELL SIGNALLING PATHWAYS AND PROTEINS

BACKGROUND OF THE INVENTION

The Rho GTPases (Rac, Cdc42Hs and Rho) are implicated in the regulation of diverse biological responses including transcriptional activation, growth control and the reorganization of cell morphology. (Hall et al., Science, 1998, 279:509-514 and Van Aelst et al., Genes Dev., 1997, 11: 2295-2322) Microinjection of these GTPases into mammalian cells demonstrated that Cdc42Hs is implicated in the formation of filopodia (Nobes et al., Cell, 1995, 81: 53-62 and Kozma et al., Mol Cell Biol., 1995, 15: 1942-1952) and activation of Rac to induce lamellipodia (Ridley et al., Cell, 1992, 70: 401-410) and subsequently activates Rho to induce stress fibers (Ridley et al., Cell, 1992, 70: 401-410). Over the last few years, various down stream molecular targets have been identified for these GTPases. These targets interact with the activated GTP bound forms of the GTPases. Cdc42Hs and Rac have been shown to interact specifically with WASP (Aspenstrom et al., Curr Biol., 1996, 6: 70-75; Symons et al., Cell, 1996, 84: 723-734; and Kolluri et al., Proc Natl Acad Sci., 1996, 93: 6515-5618), IQGAP (Hart et al., EMBO J., 1996, 15: 2997-3005; and Kurodas et al., J. Bio. Chem., 1996, 271: 23363-23367), POSH (Tapon et al., EMBO J., 1998, 17: 1395-1404), POR1 (Van Aelst et al., EMBO J 1996, 115: 3778-3786) p67-phox (Diekmann et al., Science,1994, 265: 531-533), MLK3 (Teramoto et al, J Biol Chem., 1996, 271: 27225-27228) and PAKs (Maser et al., Nature, 1993, 363: 364-357; Martin et al., EMBO J 1995, 14: 1997-1978; and Bagrodia et al., J Biol Chem., 1995, 270: 27995-27998). The p21 activated kinase (PAK) is one of the downstream effectors for the GTPases Rae and Cdc42Hs (Maser et al., Nature 1993, 363: 364-357; Martin et al., EMBO J 1995, 14: 1997-1978; Bagrodia et al., J Biol Chem 1995, 270: 27995-27998; and Sells et al., Trends Cell Biol 1997, 7: 1623-167). The GTP bound form of the GTPases interacts with PAK through a conserved GTPase binding domain (GBD) and subsequently stimulates Pak activity (Maser et al., Nature 1993, 363: 364-357; Martin et al., EMBO J 1995, 14: 1997-1978; Bagrodia et al., J Biol Chem 1995, 270: 27995-27998; and Sells et al., Trends Cell Biol 1997, 7: 1623-167). Three mammalian PAKs have been identified including PAK1, 2 mouse PAK3 and three rat homologues PAK, alpha, beta, and gamma (Sells et al., Trends Cell Biol 1997, 7: 1623-167).

All of the PAKs contain a regulatory domain (PakR) and a highly conserved kinase domain that is closely related to yeast STE20 (Sells et al., Trends Cell Biol 1997, 7: 1623-167). The PakR contains the GBD and a polyproline sequence important for interaction with SH3 domain containing proteins (Bagrodia et al., J Biol Chem 1995, 270: 27995-27998. A possible role for PAK function came from studies of the yeast homologue STE20, a protein kinase that is implicated in the activation of the MAP kinase cascade in *Saccharomyces cerevisiae*. Several groups have shown that mammalian PAK can activate the JNK MAP kinase cascade (Minden et al., Cell 1995, 81: 147-1157 and Coso et al., Cell 1995, 81: 1137-1146) and recent work with effector mutants of Rac and Cdc42Hs suggests that PAK is necessary for JNK activation (Lamarche et al., Cell 1996, 87: 519-529). The fact that PAKs are effectors for Rae and Cdc42Hs suggested that they may also play a role in the regulation of the reorganization of the actin cytoskeleton. Several reports have demonstrated the recruitment of PAK to the focal complexes and lamellipodia, however, these effects are independent of PAK kinase activity and interaction with Cdc42Hs or Rae (Dharmawardhane et al., J Cell Biol 1997, 138: 1265-1278; Sells et al., Curr Biol 1997, 7: 202-210 and Manser et al., Mol Cell Biol 1997, 17: 1129-1143). Moreover, effector mutants of Rac and Cdc42Hs that fail to interact with PAKs are able to promote the induction of lamellipodia and filopodia (Lamarche et al., Cell 1996, 87: 519-529).

Pak2 interacts with the SH3 domains of NCK (Bagrodia et al., J Biol Chem 1995, 270: 27995-27998) and Grb2 through its proline rich sequence. Recently, Manser et al., Mol Cell 1998, 1: 183-192 demonstrated that PakR contains a unique proline sequence that can bind an SH3 domain of a novel GTP/GDP exchange factors-PIX. It is suggested that PIX/PAK interaction is important for the association of PAK with the focal complexes (Manser et al., Mol Cell 1998, 1: 183-192).

DESCRIPTION OF THE INVENTION

The present invention relates to nucleic acids, polypeptides, and fragments thereof, of a novel class of cell signaling proteins which interact with protein kinases and which resemble members of the Rho family. The invention especially relates to a novel protein, Chp, a cell signal transduction molecule, which regulates PAK and JNK activity, interacts with the JNK MAP kinase cascade, modulates cytoskeletal activity, and regulates gene transcription.

The invention further relates to methods of using such nucleic acids and polypeptides in therapeutics, diagnostics, and research. For example, the nucleic acids and polypeptides of Chp can be utilized in methods to identify modulators of its activity and to develop animal models to mimic human disease. The invention also concerns ligands of Chp, such as polypeptides, antibodies, and nucleic acid aptamers.

BRIEF DESCRIPTION OF THE DRAWINGS

FIG. 1 shows a nucleotide (SEQ ID NO:1) and amino sequence (SEQ ID NO:2) coding for full-length rat Chp.

FIG. 2 shows a comparison between Chp (SEQ ID NO: 3), Cdc42 (SEQ ID NO: 4), and Rac1 (SEQ ID NO: 5).

DETAILED DESCRIPTION OF THE INVENTION

Novel nucleic acid (e.g., SEQ ID NO:1) and polypeptide (e.g., SEQ ID NO:2) sequences have been identified which code for Chp, a novel class of proteins related to Cdc42Hs. Chp has one or more of the following biological activities: a PAK regulatory domain binding activity, a PAK kinase stimulatory activity, a JNK kinase stimulatory activity, a GTPase activity, a GTP/GDP binding activity, a cytoskeletal-reorganizing activity, a golgi-targeting and retention signal activity, an activity in regulating the supply of vesicles containing the components necessary for the reorganization of the cytoskeleton, or a Chp-specific immunogenic activity.

A PAK regulatory binding domain activity means, e.g., that full-length Chp, or a biologically-active polypeptide fragment thereof, interacts (e.g., binds or attaches to) with a polypeptide sequence of the PAK (p21 activated kinase) family of downstream effectors for the Rho family of GTPases, such as Rac and Cdc42Hs. In a preferred embodiment, the regulatory domain is PakR (or "PakR regulatory domain"), a highly conserved kinase domain that is related to yeast STE20 and which is obtainable from PAK2. See, e.g., Manser, E., Leun, T., Salihuddin, H., Tan, L., and Lim, L, A non-receptor tyrosine kinase that inhibits the GTPase activity of p21cdc42, Nature, 1993, 363: 364-367; Martin, G. A., Bollag, G., McCormick, F., and Abo, A, A novel serine kinase activated by rac1/CDC42Hs-dependent autophosphorylation is related to PAK65 and STE20, EMBO J 1995, 14: 1970-1978; Bagrodia, S., Derijard, B., Davis, R. J., and Cerione, R. A., Cdc42 and PAK-mediated signaling leads to Jun kinase and p38 mitogen-activated protein kinase activation, J Biol Chem 1995, 270: 27995-27998; Sells, M. A., and Chernof, J., Emerging from the Pak: the p21-activated protein kinase family, Trends Cell Biol 1997, 7: 162-167.

PakR can comprise a GTPase binding domain (GBD) and a polyproline sequence. See, e.g., Bagrodia et al., J Biol Chem 1995, 270: 27995-27998. The Chp binding domain activity can be effective to bind to PakR and stimulate PAK kinase activity, e.g., an agonist; or, it can result in binding of a Chp polypeptide to PakR, without stimulating PAK kinase activity, e.g., an antagonist. Analogously, Chp can have a JNK regulatory binding domain activity, either directly to JNK or to an intermediate. Even more generically, Chp can have a binding activity and/or stimulatory activity towards other proteins, including proteins related to PAK, JNK, MAP kinases, or synthetic polypeptides derived from them.

Binding activity can be measured conventionally. For instance, a competition binding assay can be employed to identify a compound, such as a polypeptide or antibody, which attaches to a Chp polypeptide, or a derivative thereof. A Chp polypeptide, a PakR regulatory domain, and a compound (a ligand) which is to be tested for substrate binding activity, can be combined under conditions effective for binding to occur. The assay can be accomplished in liquid phase, where bound and free ligands are separated by a membrane, or, an assay can be accomplished in solid phase, as desired. Solid-phase assays can be performed using high through-put procedures, e.g., on chips, wafers, etc. Cellular-based functional assays can also be used, e.g., as described in the examples below where Chp is fused in-frame to a plasma membrane targeting signal and PakR is fused in-frame to Ras, and effective binding between it and a Chp polypeptide results in rescue of cell viability.

A "PAK kinase stimulatory activity" means, e.g., an ability of a full-length Chp, or a biologically-active fragment thereof, to produce, or result, in, a protein kinase activity of a member of the PAK family. As explained below and in the examples, stimulatory activity can be mediated, for example, through a normal Chp or an activated Chp. Activation can be achieved in vivo, or it can be achieved by altering the amino acid sequence of Chp. The stimulation can be direct, or it can, be indirect. For instance, it is generally believed that GTP bound forms of the GTPases interact with the PAK, and other kinases, family through a conserved GTPase binding domain (GBD) and polyproline sequence. When this interaction is "effective," kinase activity is stimulated. While not being bound by any theory, a mechanism through which Chp can produce or stimulate kinase activity in a PAK can be through binding of Chp to a specific domain in PAK, such as PakR. Thus, PAK stimulatory activity can involve direct binding to PAK. As mentioned about, binding activity can be dissociated from kinase stimulatory activity.

A JNK kinase stimulatory activity means, e.g., e.g., an ability of a full-length Chp, or a biologically-active fragment thereof, to produce, result in, or induce, a protein kinase activity of the JNK and/or p38 MAP kinase pathway. Minden et al., Cell, 81: 1147-1157, 1995; Coso et al., Cell, 81: 1137-1146, 1995. This stimulatory activity is more selective for JNK, than ERK or p38, i.e., Chp does not significantly induce p38 or ERK kinase activity. A normal Chp polypeptide as shown in FIG. 1 (SEQ ID NO:2) or an activated form of Chp polypeptide can induce kinase activity in the JNK MAP kinase pathway. Activation of the JNK pathway can be mediated through PAKs.

Kinase activity can be measured as described in the examples below, conventionally, e.g., as disclosed in Bagrodia et al., J. Biol. Chem., 270:27995-27998, 1995; Coso et al., Cell, 81:1137-1146, 1995.

A full-length Chp, or a biologically-active polypeptide fragment thereof, can also have a GTP/GDP binding and/or a GTPase activity. These activities can be measured routinely as described in the mentioned references. See, also, Boume et al., Nature, 349:117-127, 1991.

Additionally, a full-length Chp, or a biologically-active polypeptide fragment thereof, can have a cytoskeletal-reorganizing activity. Such activity means, e.g., an ability of Chp polypeptides, especially activated Chp, to regulate the polymerization of the actin cytoskeleton of cells, including the production of focal complexes, focal complexes at the plasma membrane, adhesion fibers, stress fibers, lamellipodia, and filopodia. See, e.g., Nobes and Hall, *Cell,* 81:53-62, 1995; Symons et al., *Cell,* 84: 723-734. This activity can be measured routinely, e.g., by visualizing the cytoskeleton using conventional reagents, after introduction of a Chp, or a nucleic acid coding for it, into a target cell. See, also, examples below.

By the term "Chp-specific immunogenic activity", it is meant that the Chp polypeptide elicits an immunological response which is selective for Chp. Such response can be cellular or humoral. Thus, the stimulation of antibodies, T-cells, macrophages, B-cells, dendritic cells, etc., by a Chp amino acid sequence selected from a mammalian Chp polypeptide, e.g., rat as shown in FIG. 1 (SEQ ID NO:2), is a specific immunogenic activity. These responses can be measured routinely. See, for example, below where Chp-specific antibodies were generated against a C-terminus peptide conjugated to KLH.

A mammalian Chp, such as a rat Chp, is a mammalian polypeptide having an amino acid sequence which is obtainable from a natural source and which has one or more of the mentioned activities. It can be full-length (i.e., as shown in FIG. 1 (SEQ ID NO:2), having an amino acid sequence which begins with an initiation codon and ends with a stop codon) or it can be less than full-length and be biologically-active. It therefore includes naturally-occurring normal, mutant, polymorphic, etc., sequences. Natural sources include, e.g., living cells, e.g., obtained from tissues or whole organisms, cultured cell lines, including primary and immortalized cell lines, biopsied tissues, etc.

The present invention also relates to fragments of a full-length mammalian Chp. The fragments are preferably "biologically active". By "biologically active", it is meant that the polypeptide fragment possesses an activity in a living system or with components of a living system. Biological activities include those mentioned, e.g., a PAK regulatory domain binding activity, a PAK kinase stimulatory activity, a JNK kinase stimulatory activity, a GTPase activity, a GTP binding activity, a cytoskeletal-reorganizing activity, or a Chp-specific immunogenic activity. Fragments can be prepared according to any desired method, including, chemical synthesis, genetic engineering, cleavage products, etc. See, below. A biological-fragment of Chp includes a Chp which has had amino acid sequences removed or modified at either the carboxy- or amino-terminus of the protein, e.g., processing to a "mature" Chp from its pro-form.

The present invention also relates to a rat Chp having a deduced sequence of amino acids 1 to 236 amino acids as shown in FIG. 1 (SEQ ID NO: 2). The 236 amino acid polypeptide has a molecular weight of about 36 kilodaltons. It comprises the following domains: a unique Chp domain at about amino acids 1-32 (SEQ ID NO: 6); a GTPase domain related to CDC42 and Rac GTPases at amino acids 32-211 (SEQ ID NO: 7); a PAK regulatory binding domain activity (involving direct binding or conformational effects) at about amino acid 211-236 (SEQ ID NO: 8).

A Chp polypeptide of the invention, e.g., having an amino acid sequence as shown in FIG. 1 (SEQ ID NO: 2), can be analyzed by available methods to identify other structural and/or functional domains in the polypeptide, including membrane spanning regions, hydrophobic regions. For example, a Chp polypeptide can be analyzed by methods disclosed in, e.g., Kyte and Doolittle, *J. Mol. Bio.*, 157:105, 1982; EMBL Protein Predict; Rost and Sander, *Proteins*, 19:55-72, 1994.

Other Chp homologs from mammalian and non-mammalian sources can be obtained according to various methods. For example, hybridization with an oligonucleotide selected from the nucleotide sequence of a human Chp can be employed to select homologs from other species, e.g., as described in Sambrook et al., *Molecular Cloning*, 1989, Chapter 11. Such homologs can have varying amounts of nucleotide and amino acid sequence identity and similarity to Chp. Mammalian organisms include, e.g., rodents, mouse, rats, hamsters, monkeys, pigs, cows, etc. Non-mammalian organisms include, e.g., vertebrates, invertebrates, zebra fish, chicken, *Drosophila, C. elegans, Xenopus, S. pombe, S. cerevisiae*, roundworms, prokaryotes, plants, *Arabidopsis*, viruses, etc.

The invention also relates to Chp specific amino acid sequences, e.g., a defined amino acid sequence which is found in the particular rat sequence of FIG. 1 (SEQ ID NO: 2), but not in other amino acid sequences from non-Chp polypeptides. See, also, FIG. 2 (SEQ ID NQ:3, SEQ ID NQ:4, SEQ ID NQ:5), where comparisons between related proteins can be used to select sequences specific for Chp. A specific amino acid sequence can be found routinely, e.g., by searching a gene/protein database using the BLAST set of computer programs. A Chp specific amino acid sequence can be useful to produce peptides as antigens to generate an immune response specific for it. Antibodies obtained by such immunization can be used as a specific probe for a mammalian Chp protein for diagnostic or research purposes. Chp specific amino acid sequences include, e.g., amino acids 4-32, 216-234, 216-224, and 229-234, as set forth in FIG. 1 (SEQ ID NO: 2).

As mentioned, polypeptides of the present invention can comprise a complete amino acid sequence for a Chp (i.e., full-length as determined from a nucleotide sequence having a start and stop codon), a mature amino acid sequence (i.e., where the Chp polypeptide is produced as a precursor which is processed into a mature polypeptide, analogously to the peptide processing that occurs to Ras (e.g., Gelb, *Science*, 275: 1750-1751, 1997), or fragments thereof. Useful fragments include, e.g., fragments comprising, or consisting essentially of, any of the aforementioned domains and Chp specific amino acid sequences.

A fragment of a Chp polypeptide can be selected to have a specific biological activity, e.g., a PAK regulatory domain binding activity, a PAK kinase stimulatory activity, a JNK kinase stimulatory activity, a GTPase activity, a GTP binding activity, a cytoskeletal-reorganizing activity, or a Chp-specific immunogenic activity. A useful fragment can be identified routinely by testing such fragments for a desired activity. The measurement of these activities is described below and in the examples. These peptides can also be identified and prepared as described in EP 496 162. A useful fragment can comprise, or consist essentially of, e.g., about nine contiguous amino acids, preferably about 10, 15, 20, or 30 contiguous amino acids of FIG. 1 (SEQ ID NO: 2).

A polypeptide of the present invention can also have 100% or less amino acid sequence identity to the amino acid sequence set forth in FIG. 1 (SEQ ID NO:2). For the purposes of the following discussion: Sequence identity means that the same nucleotide or amino acid which is found in the sequence set forth in FIG. 1 (nucleotide sequence SEQ ID NO:1; amino acid sequence SEQ ID NO:2) is found at the corresponding position of the compared sequence(s) (e.g., SEQ ID NOS: 3-5). A polypeptide having less than 100% sequence identity to the amino acid sequence set forth in FIG. 1 (SEQ ID NO:2) can contain various substitutions from the naturally-occurring sequences, including homologous and non-homologous amino acid substitutions. See below for examples of homologous amino acid substitution. The sum of the identical and homologous residues divided by the total number of residues in the sequence over which the Chp polypeptide is compared is equal to the percent sequence similarity. For purposes of calculating sequence identity and similarity, the compared sequences can be aligned and calculated according to any desired method, algorithm, computer program, etc., including, e.g., FASTA, BLASTA. A polypeptide having less than 100% amino acid sequence identity to the amino acid sequence of FIG. 1 (SEQ ID NO: 2) can have about 99%, 98%, 97%, 95%, 90%, 70%, or as low as about 53% sequence identity. A preferred amount of amino acid sequence identity is about 87% or more, e.g., about 88%, 89%. See, below for discussion of mutations or muteins.

The present invention also relates to Chp polypeptide muteins, i.e., any polypeptide which has an amino acid sequence which differs in amino acid sequence from an amino acid sequence obtainable from a natural source (a fragment of a mammal Chp does not differ in amino acid sequence from a naturally-occurring Chp). Thus, Chp muteins comprise amino acid substitutions, insertions, and deletions, including non-naturally occurring amino acids.

Muteins to a Chp amino acid sequence of the invention can also be prepared based on homology searching from gene data banks, e.g., Genbank, EMBL. Sequence homology searching can be accomplished using various methods, including algorithms described in the BLAST family of computer programs, the Smith-Waterman algorithm, etc. A mutein(s) can be introduced into a sequence by identifying and aligning amino acids within a domain which are identical and/or homologous between polypeptides and then modifying an amino acid based on such alignment. For instance, sequence comparisons between Chp, Cdc-42, and Rac1 are shown in FIG. 2 (SEQ ID NO:3, SEQ ID NO:4, SEQ ID NO:5). These alignments reveal amino acid positions which are both identical and different from each other, providing information on amino acid substitutions that would be expected to reduce, decrease, or, eliminate a biological activity of Chp. For instance, where alignment reveals identical amino acids conserved between two or more domains (e.g., replacing the conserved residues in FIG. 1 (SEQ ID NO: 2), elimination or substitution of the amino acid(s) would be expected to adversely affect its biological activity.

Amino acid substitution can be made by replacing one homologous amino acid for another. Homologous amino acids can be defined based on the size of the side chain and degree of polarization, including, small nonpolar: cysteine, proline, alanine, threonine; small polar: serine, glycine, aspartate, asparagine; large polar: glutamate, glutamine, lysine, arginine; intermediate polarity: tyrosine, histidine, tryptophan; large nonpolar: phenylalanine, methionine, leucine, isoleucine, valine. Homologous acids can also be grouped as follows: uncharged polar R groups, glycine, serine, threonine, cysteine, tyrosine, asparagine, glutamine; acidic amino acids (negatively charged), aspartic acid and glutamic acid; basic amino acids (positively charged), lysine, arginine, histidine. Homologous amino acids also include those described by Dayhoff in the *Atlas of Protein Sequence and Structure* 5 (1978), and by Argos in *EMBO J.*, 8, 779-785 (1989).

Muteins in accordance with the present invention include amino acid sequences where a residue in the Chp sequence is replaced by a homologous residue from a corresponding domain of Cdc42 or Rac1. See, e.g., FIG. 2 (SEQ ID NO:4, SEQ ID NO:5).

Thus, the present invention relates to a Chp nucleotide sequence of FIG. 1 (SEQ ID NO: 1), wherein said nucleic acid codes for a polypeptide and one or more amino acid positions are substituted or deleted, or both, and the polypeptide coded for by the nucleic acid has a PAK regulatory domain binding activity, a PAK kinase stimulatory activity, a JNK kinase stimulatory activity, a GTPase activity, a GTP binding activity, a cytoskeletal-reorganizing activity, or a Chp-specific immunogenic activity. For instance, a Chp polypeptide mutein, and its corresponding nucleotide coding sequence, can have an amino acid sequence as set forth in FIG. 1 (SEQ ID NO: 2), except where one or more positions are substituted by homologous amino acids, e.g., where there are 1, 5, 10, 15, or 20 substitutions. The invention also relates to mutein polypeptides and mutein nucleic acids coding for such polypeptides. How a modification affects the mentioned activities can be measured according to the methods described above, below, and as the skilled worker in the field would know.

As mentioned, amino acid substitutions can also be made based on analogy to related proteins, such as Cdc42 and Rac1. For instance, replacement of glycine at amino acid 40 with valine (G40V), results in a constitutively active or an activated form of Chp. By the term "activated form of a human Chp polypeptide, or biologically-active fragments thereof," it is meant a human Chp polypeptide have a naturally-obtainable sequence which can be a naturally-occurring mutation having constitutive activity or a naturally-obtainable sequence which has been modified to produce a constitutively active polypeptide. An example of modified a polypeptide is the above-mentioned G40V mutation. By the terms "constitutively active" or "activated", it is meant a polypeptide sequence, and modifications thereof, which are in a "turned-on" state. In the context of JNK stimulatory activity, an activated form of a human Chp polypeptide, or a fragment thereof, would be a polypeptide that stimulates the JNK kinase pathway. The G40V mutation is such an example. Other mutations could be selected routinely by modifying or mutating Chp, and selecting for those mutations which stimulate the JNK pathway, e.g., by measuring kinase activity according to the methods and examples described below.

Another mutation which can be prepared is replacement of the serine at amino acid 45 to an asparagine (S45D) This mutation results in a dominant, negative allele, locked in the GDP bound inactive form. Such mutation results in an inactive Chp, as compared to the G40V mutation. These substitutions, and others, were introduced based on homology to Cdc42 and other Rho GTPases. Thus, guidance for making mutations can be based on these homologies; selecting for desired activities, such as enhanced, activated, reduced, inactive, etc., can be assayed routinely as described in the methods and examples below.

A mammalian Chp full-length polypeptide, fragment, or substituted polypeptide can also comprise various modifications, where such modifications include lipid modification, methylation, phosphorylation, glycosylation, covalent modifications (e.g., of an R-group of an amino acid), amino acid substitution, amino acid deletion, or amino acid addition. Modifications to the polypeptide can be accomplished according to various methods, including recombinant, synthetic, chemical, etc.

Polypeptides of the present invention (e.g., human Chp, fragments thereof, mutations thereof) can be used in various ways, e.g., in assays, as immunogens for antibodies as described below, as biologically-active agents (e.g., having one or more of the activities associated with Chp).

A polypeptide coding for a Chp, a derivative thereof, or a fragment thereof, can be combined with one or more structural domains, functional domains, detectable domains, antigenic domains, and/or a desired polypeptide of interest, in an arrangement which does not occur in nature, i.e., not naturally-occurring, e.g., as in a human or Chp gene, a genomic fragment prepared from the genome of a living organism, e.g., an animal, preferably a mammal, such as human, mouse, or cell lines thereof. A polypeptide comprising such features is a chimeric or fusion polypeptide. Such a chimeric polypeptide can be prepared according to various methods, including, chemical, synthetic, quasi-synthetic, and/or recombinant methods. A chimeric nucleic acid coding for a chimeric polypeptide can contain the various domains or desired polypeptides in a continuous (e.g., with multiple N-terminal domains to stabilize or enhance activity) or interrupted open reading frame, e.g., containing introns, splice sites, enhancers, etc. The chimeric nucleic acid can be produced according to various methods. See, e.g., U.S. Pat. No. 5,439,819. A domain or desired polypeptide can possess any desired property, including, a biological function such as signaling, growth promoting, cellular targeting (e.g., signal sequence, targeting sequence, such as targeting to the golgi or endoplasmic reticulum), etc., a structural function such as hydrophobic, hydrophilic, membrane-spanning, etc., receptor-ligand functions, and/or detectable functions, e.g., combined with enzyme, fluorescent polypeptide, green fluorescent protein, (Chalfie et al., 1994, *Science*, 263:802; Cheng et al., 1996, *Nature Biotechnology*, 14:606; Levy et al., 1996, *Nature Biotechnology*, 14:610, etc. In addition, a polypeptide, or a part of it, can be used as a selectable marker when introduced into a host cell. For example, a nucleic acid coding for an amino acid sequence according to the present invention can be fused in-frame to a desired coding sequence and act as a tag for purification, selection, or marking purposes. The region of fusion can encode a cleavage site to facilitate expression, isolation, purification, etc.

A polypeptide according to the present invention can be produced in an expression system, e.g., in vivo, in vitro, cell-free, recombinant, cell fusion, etc., according to the present invention. Modifications to the polypeptide imparted by such systems include glycosylation, amino acid substitution (e.g., by differing codon usage), polypeptide processing such as digestion, cleavage, endopeptidase or exopeptidase activity, attachment of chemical moieties, including lipids and phosphates, etc.

A polypeptide according to the present invention can be recovered from natural sources, transformed host cells (culture medium or cells) according to the usual methods, including, detergent extraction (e.g., CHAPS, octylglucoside), ammonium sulfate or ethanol precipitation, acid extraction, anion or cation exchange chromatography, phosphocellulose chromatography, hydrophobic interaction chromatography, hydroxyapatite chromatography and lectin chromatography. Protein refolding steps can be used, as necessary, in completing the configuration of the mature protein. Finally, high performance liquid chromatography (HPLC) can be employed for purification steps. A Chp polypeptide can also be isolated as described for GTPases as would be known in the art.

A mammalian Chp nucleic acid, or fragment thereof, is a nucleic acid having a nucleotide sequence obtainable from a natural source. See, above. It therefore includes naturally-occurring, normal, mutant, polymorphic alleles, etc. Natural sources include, e.g., living cells obtained from tissues and whole organisms, cultured cell lines, including primary and immortalized cell lines.

Rat Chp is expressed as a single mRNA species of about 1.5 kb. It is most abundant in brain and testes, with lower amounts expressed in the spleen and lung. Consequently, Chp can be used as a marker for the presence of brain and testes, in tissue sections (using Chp-specific antibodies or Chp-specific nucleic acid probes), in biopsied samples, etc.

A nucleic acid sequence of a rat allele of a mammalian Chp is shown in FIG. 1 (SEQ ID NO:1). It contains an open-reading frame of 236 amino acids (SEQ ID NO:2). It contains both 5' untranslated sequence and 3' untranslated sequences as shown in FIG. 1 (SEQ ID NO:1, SEQ ID NO:2). A nucleic acid sequence of the invention can contain the complete coding sequence from amino acid 1 to amino acid 236, degenerate sequences thereof, and fragments thereof. A nucleic acid according to the present invention can also comprise a nucleotide sequence which is 100% complementary, e.g., an anti-sense, to any nucleotide sequence mentioned above and below.

A nucleic acid according to the present invention can be obtained from a variety of different sources. It can be obtained from DNA or RNA, such as polyadenylated mRNA, e.g., isolated from tissues, cells, or whole organism. The nucleic acid can be obtained directly from DNA or RNA, or from a cDNA library. The nucleic acid can be obtained from a cell at a particular stage of development, having a desired genotype, phenotype (e.g., an embryonic or adult heart cell or tissue), etc.

As described for Chp polypeptides mentioned above, a nucleic acid comprising a nucleotide sequence coding for a polypeptide according to the present invention can include only coding sequence; a coding sequence and additional coding sequence (e.g., sequences coding for leader, secretory, targeting, enzymatic, fluorescent or other diagnostic peptides), coding sequences and non-coding sequences, e.g., untranslated sequences at either a 5' or 3' end, or dispersed in the coding sequence, e.g., introns. A nucleic acid comprising a nucleotide sequence coding without interruption for a polypeptide means that the nucleotide sequence contains an amino acid coding sequence for a Chp, with no non-coding nucleotides interrupting or intervening in the coding sequence, e.g., absent intron(s). Such a nucleotide sequence can also be described as contiguous. A genomic DNA coding for a human or other mammalian Chp, etc., can be obtained routinely.

A nucleic acid according to the present invention also can comprise an expression control sequence operably linked to a nucleic acid as described above. The phrase Aexpression control sequence≅means a nucleic acid sequence which regulates expression of a polypeptide coded for by a nucleic acid to which it is operably linked. Expression can be regulated at the level of the mRNA or polypeptide. Thus, the expression control sequence includes mRNA-related elements and protein-related elements. Such elements include promoters, enhancers (viral or cellular), ribosome binding sequences, transcriptional terminators, etc. An expression control sequence is operably linked to a nucleotide coding sequence when the expression control sequence is positioned in such a manner to effect or achieve expression of the coding sequence. For example, when a promoter is operably linked 5' to a coding sequence, expression of the coding sequence is driven by the promoter. Expression control sequences can be heterologous or endogenous to the normal gene.

A nucleic acid in accordance with the present invention can be selected on the basis of nucleic acid hybridization. The ability of two single-stranded nucleic acid preparations to hybridize together is a measure of their nucleotide sequence complementarity, e.g., base-pairing between nucleotides, such as A-T, G-C, etc. The invention thus also relates to nucleic acids, and their complements, which hybridize to a nucleic acid comprising a nucleotide sequence as set forth in FIG. 1 (SEQ ID NO: 1). A nucleotide sequence hybridizing to the latter sequence will have a complementary nucleic acid strand, or act as a template for one in the presence of a polymerase (i.e., an appropriate nucleic acid synthesizing enzyme). The present invention includes both strands of nucleic acid, e.g., a sense strand and an anti-sense strand.

Hybridization conditions can be chosen to select nucleic acids which have a desired amount of nucleotide complementarity with the nucleotide sequence set forth in FIG. 1 (SEQ ID NO: 1). A nucleic acid capable of hybridizing to such sequence, preferably, possesses, e.g., about 85%, more preferably, 90%, 92%, and even more preferably, 95%, 97%, or 100% complementarity, between the sequences. The present invention particularly relates to nucleic acid sequences which hybridize to the nucleotide sequence set forth in FIG. 1 (SEQ ID NO. 1) under low or high stringency conditions.

Nucleic acids which hybridize to Chp sequences can be selected in various ways. For instance, blots (i.e., matrices containing nucleic acid), chip arrays, and other matrices comprising nucleic acids of interest, can be incubated in a prehybridization solution (6×SSC, 0.5% SDS, 100 µg/ml denatured salmon sperm DNA, 5× Denhardt's solution, and 50% formamide), at 30EC, overnight, and then hybridized with a detectably Chp probe (see below) in a hybridization solution (e.g., 6×SSC, 0.5% SDS, 100 µg/ml denatured salmon sperm DNA and 50% formamide), at 42EC, overnight in accordance with known procedures. Blots can be washed at high stringency conditions that allow, e.g., for less than 5% bp mismatch (e.g., wash twice in 0.1% SSC and 0.1% SDS for 30 min at 65SEC), i.e., selecting sequences having 95% or greater sequence identity. Other non-limiting examples of high stringency conditions includes a final wash at 65EC in aqueous buffer containing 30 mM NaCl and 0.5% SDS. Another example of high stringent conditions is hybridization in 7% SDS, 0.5 M $NaPO_4$, pH 7, 1 mM EDTA at 50EC, e.g., overnight, followed by one or more washes with a 1% SDS solution at 42EC. The activated Chp and dominant negative Chp sequences described herein hybridize to the wild-type nucleic acid sequence in FIG. 1 (SEQ ID NO: 1), and oligonucleotide probes thereof, under the aforementioned high stringency conditions. Whereas high stringency washes can allow for less than 5% mismatch, relaxed or low stringency wash conditions (e.g., wash twice in 0.2% SSC and 0.5% SDS for 30 mm at 37EC) can permit up to 20% mismatch. Another non-limiting example of low stringency conditions includes a final wash at 42EC in a buffer containing 30 mM NaCl and 0.5% SDS.

Washing and hybridization can also be performed as described in Sambrook et al., *Molecular Cloning*, 1989, Chapter 9. Hybridization can also be based on a calculation of melting temperature (Tm) of the hybrid formed between the probe and its target, as described in Sambrook et al., Stringent conditions can be selected to isolate sequences, and their complements, which have, e.g., at least about 95%, preferably 97%, nucleotide complementarity between the probe (e.g., an oligonucleotide of Chp) and target nucleic acid (a Chp mutein or homolog).

According to the present invention, a nucleic acid or polypeptide can comprise one or more differences in the nucleotide or amino acid sequence set forth in FIG. 1 (SEQ ID NOS: 1-2). Changes or modifications to the nucleotide and/or amino acid sequence can be accomplished by any method available, including directed or random mutagenesis.

A nucleic acid coding for a rat Chp according to the invention can comprise nucleotides which occur in a naturally-occurring Chp gene e.g., naturally-occurring polymorphisms, normal or mutant alleles (nucleotide or amino acid), mutations which are discovered in a natural population of mammals, such as humans, monkeys, pigs, mice, rats, or rabbits. By the term naturally-occurring, it is meant that the nucleic acid is obtainable from a natural source, e.g., animal tissue and cells, body fluids, tissue culture cells, forensic samples. Naturally-occurring mutations can include deletions (e.g., a truncated amino- or carboxy-terminus), substitutions, inversions, or additions of nucleotide sequence. These genes can be detected and isolated by nucleic acid hybridization according to methods which one skilled in the art would know. A nucleotide sequence coding for a rat Chp polypeptide of the invention can contain codons found in a naturally-occurring gene, transcript, or cDNA, for example, e.g., as set forth in FIG. 1 (SEQ ID NO:1), or it can contain degenerate codons coding for the same amino acid sequences. For instance, it may be desirable to change the codons in the sequence to optimize the sequence for expression in a desired host.

A nucleic acid according to the present invention can comprise, e.g., DNA, RNA, synthetic nucleic acid, peptide nucleic acid, modified nucleotides, or mixtures. A DNA can be double- or single-stranded. Nucleotides comprising a nucleic acid can be joined via various known linkages, e.g., ester, sulfamate, sulfamide, phosphorothioate, phosphoramidate, methylphosphonate, carbamate, etc., depending on the desired purpose, e.g., resistance to nucleases, such as RNAase H, improved in vivo stability, etc. See, e.g., U.S. Pat. No. 5,378,825.

Various modifications can be made to the nucleic acids, such as attaching detectable markers (avidin, biotin, radioactive elements), moieties which improve hybridization, detection, or stability. The nucleic acids can also be attached to solid supports, e.g., nitrocellulose, magnetic or paramagnetic microspheres (e.g., as described in U.S. Pat. No. 5,411,863; U.S. Pat. No. 5,543,289; for instance, comprising ferromagnetic, supermagnetic, paramagnetic, superparamagnetic, iron oxide and polysaccharide), nylon, agarose, diazotized cellulose, latex solid microspheres, polyacrylamides, etc., according to a desired method. See, e.g., U.S. Pat. Nos. 5,470,967; 5,476,925; 5,478,893.

Another aspect of the present invention relates to oligonucleotides or nucleic acid probes. Such oligonucleotides or nucleic acid probes can be used, e.g., to detect, quantitate, or isolate a mammalian Chp nucleic acid in a test sample, or to identify Chp homologs. In a preferred embodiment, the nucleic acids can be utilized as oligonucleotide probes, e.g., in PCR, differential display, in combination with cDNA libraries, expression libraries, etc. Detection can be desirable for a variety of different purposes, including research, diagnostic, and forensic. For diagnostic purposes, it may be desirable to identify the presence or quantity of a nucleic acid sequence in a sample, where the sample is obtained from tissue, cells, body fluids, etc. In a preferred method, the present invention relates to a method of detecting a nucleic acid comprising, contacting a target nucleic acid in a test sample with an oligonucleotide under conditions effective to achieve hybridization between the target and oligonucleotide; and detecting hybridization. An oligonucleotide in accordance with the invention can also be used in synthetic nucleic acid amplification such as PCR (e.g., Saiki et al., 1988, *Science*, 241:53; U.S. Pat. No. 4,683,202; *PCR Protocols: A Guide to Methods and Applications*, Innis et al., eds., Academic Press, New York, 1990) or differential display (See, e.g., Liang et al., *Nucl. Acid. Res.*, 21:3269-3275, 1993; U.S. Pat. No. 5,599,672; WO97/18454). Such detection can be accomplished in combination with oligonucleotides for other genes, e.g., genes involved in stress fiber formation, signal transduction, growth, cancer, any of the genes mentioned above or below, etc. Oligonucleotides can also be used to test for mutations, e.g., using mismatch DNA repair technology as described in U.S. Pat. No. 5,683,877; U.S. Pat. No. 5,656,430; Wu et al., Proc. Natl. Acad. Sci., 89:8779-8783, 1992.

Oligonucleotides of the present invention can comprise any continuous nucleotide sequence of FIG. 1 (SEQ ID NO:1) or a complement thereto. These oligonucleotides (nucleic acid) according to the present invention can be of any desired size, e.g., about 10-200 nucleotides, 12-100, preferably 12-50, 12-25, 14-16, at least about 15, at least about 20, etc. The oligonucleotides can have non-naturally-occurring nucleotides, e.g., inosine, AZT, 3TC, etc. The oligonucleotides can have 100% identity or complementarity to a sequence of FIG. 1 (SEQ ID NO:1), or it can have mismatches or nucleotide substitutions, e.g., 1, 2, 3, 4, or 5 substitutions. In accordance with the present invention, the oligonucleotide can comprise a kit, where the kit includes a desired buffer (e.g., phosphate, tris, etc.), detection compositions, etc. The oligonucleotide can be labeled or unlabeled, with radioactive or non-radioactive labels as known in the art.

Another aspect of the present invention is a nucleotide sequence which is unique to rat Chp. By a unique sequence to a Chp, it is meant a defined order of nucleotides which occurs in Chp, e.g., in the nucleotide sequence of FIG. 1 (SEQ ID NO: 1), but rarely or infrequently in other nucleic acids, especially not in an animal nucleic acid, preferably mammal, such as human, rat, mouse, etc. Unique nucleotide sequences include the sequences, or complements thereto, coding for amino acids 4-32, 216-224, and 29-34. Such sequences can be used as probes in any of the methods described herein or incorporated by reference. Both sense and antisense nucleotide sequences are included. A unique nucleic acid according to the present invention can be determined routinely. A nucleic acid comprising such a unique sequence can be used as a hybridization probe to identify the presence of, e.g., human or mouse Chp, in a sample comprising a mixture of nucleic acids, e.g., on a Northern blot. Hybridization can be performed under high stringent conditions (see, above) to select nucleic acids having at least 95% identity (i.e., complementarity) to the probe, but less stringent conditions can also be used. A unique Chp nucleotide sequence can also be fused in-frame, at either its 5' or 3' end, to various nucleotide sequences as mentioned throughout the patent, including coding sequences for other parts of Chp, enzymes, GFP, etc, expression control sequences, etc.

As already discussed, hybridization can be performed under different conditions, depending on the desired selectivity, e.g., as described in Sambrook et al., *Molecular Cloning*, 1989. For example, to specifically detect human or mouse Chp, an oligonucleotide can be hybridized to a target nucleic acid under conditions in which the oligonucleotide only hybridizes to it, e.g., where the oligonucleotide is 100% complementary to the target. Different conditions can be used if it is desired to select target nucleic acids which have less than 100% nucleotide complementarity, at least about, e.g., 99%, 97%, 95%, 90%, 70%, 67%.

Anti-sense nucleic acid can also be prepared from a nucleic acid according to the present invention, preferably an anti-sense to a coding sequence of FIG. 1 (SEQ ID NO: 1). Anti-sense nucleic acid can be used in various ways, such as to regulate or modulate expression of Chp, e.g., inhibit it, to detect its expression, or for in situ hybridization. These oligonucleotides can be used analogously to U.S. Pat. No. 5,576,208. For the purposes of regulating or modulating expression of Chp, an anti-sense oligonucleotide can be operably linked to an expression control sequence.

The nucleic acid according to the present invention can be labeled according to any desired method. The nucleic acid can be labeled using radioactive tracers such as $^{32}P$, $^{35}S$, $^{125}I$, $^{3}H$, or $^{14}C$, to mention some commonly used tracers. The radioactive labeling can be carried out according to any method such as, for example, terminal labeling at the 3' or 5' end using a radiolabeled nucleotide, polynucleotide kinase (with or without dephosphorylation with a phosphatase) or a ligase (depending on the end to be labeled). A non-radioactive labeling can also be used, combining a nucleic acid of the present invention with residues having immunological properties (antigens, haptens), a specific affinity for certain reagents (ligands), properties enabling detectable enzyme reactions to be completed (enzymes or coenzymes, enzyme substrates, or other substances involved in an enzymatic reaction), or characteristic physical properties, such as fluorescence or the emission or absorption of light at a desired wavelength, etc.

A nucleic acid according to the present invention, including oligo-nucleotides, anti-sense nucleic acid, etc., can be used to detect expression of Chp in whole organs, tissues, cells, etc., by various techniques, including Northern blot, PCR, in situ hybridization, etc. Such nucleic acids can be particularly useful to detect disturbed expression, e.g., cell-specific and/or subcellular alterations, of Chp. The levels of Chp can be determined alone or in combination with other gene products, especially brain and testes specific gene products, or other gene products involved in cell signaling and regulation, such as PAK, PAK2, JNK, Ras, Rho, etc.

A nucleic acid according to the present invention can be expressed in a variety of different systems, in vitro and in vivo, according to the desired purpose. For example, a nucleic acid can be inserted into an expression vector, introduced into a desired host, and cultured under conditions effective to achieve expression of a polypeptide coded for by the nucleic acid. Effective conditions include any culture conditions which are suitable for achieving production of the polypeptide by the host cell, including effective temperatures, pH, medusa, additives to the media in which the host cell is cultured (e.g., additives which amplify or induce expression such as butyrate, or methotrexate if the coding nucleic acid is adjacent to a dhfr gene), cycloheximide, cell densities, culture dishes, etc. A nucleic acid can be introduced into the cell by any effective method including, e.g., naked DNA, calcium phosphate precipitation, electroporation, injection, DEAE-Dextran mediated transfection, fusion with liposomes, association with agents which enhance its uptake into cells, viral transfection. A cell into which a nucleic acid of the present invention has been introduced is a transformed host cell. The nucleic acid can be extrachromosomal or integrated into a chromosome(s) of the host cell. It can be stable or transient.

An expression vector is selected for its compatibility with the host cell. Host cells include, mammalian cells (e.g., COS-7, CV1, BHK, CHO, HeLa, LTK, NIH 3T3, 293, PAE, human, human fibroblast, human primary tumor cells, testes cells), insect cells, such as Sf9 (*S. frugipeda*) and *Drosophila*, bacteria, such as *E. coli, Streptococcus, bacillus*, yeast, such as *Sacharomyces, S. cerevisiae* (e.g., cdc mutants, cdc25, cell cycle and division mutants, such as ATCC Nos. 42563, 46572, 46573, 44822, 44823, 46590, 46605, 42414, 44824, 42029, 44825, 44826, 42413, 200626, 28199, 200238, 74155, 44827, 74154, 74099, 201204, 48894, 42564, 201487, 48893, 28199, 38598, 201391, 201392), fungal cells, plant cells, embryonic stem cells (e.g., mammalian, such as mouse or human), fibroblasts, muscle cells, neuronal cells, etc. Expression control sequences are similarly selected for host compatibility and a desired purpose, e.g., high copy number, high amounts, induction, amplification, controlled expression. Other sequences which can be employed include enhancers such as from SV40, CMV, RSV, inducible promoters, cell-type specific elements, or sequences which allow selective or specific cell expression. Promoters that can be used to drive its expression, include, e.g., the endogenous promoter, promoters of other genes in the cell signal transduction pathway, MMTV, SV40, trp, lac, tac, or T7 promoters for bacterial hosts; or alpha factor, alcohol oxidase, or PGH promoters for yeast.

Another gene of interest can be introduced into the same host for purposes of, e.g., modulating Chp function. Such genes can be the normal gene, or a variation, e.g., a mutation, chimera, polymorphism, etc. Such genes include, e.g., members of the same or related signaling pathways, e.g., Ras family, Cdc42Hs, Racs, Rhos, PAKS, JNK, Jun, WASP, IQGAP, POSH, POR1, p67-phox, MLK3, MAP kinases, NCK, SOS, ERKs, p38, GEFs, GAPs, GDIs, Wiskott-Aldrich Syndrome protein, FTases, STE14, p53, Rb, Mtase, GTPases subunits, Dbl, lbc, Ost, Lsc, STATS, Raf, src, Jun, fos, elk, MEK, Ste11, Ste7, etc.

A nucleic acid or polypeptide of the present invention can be used as a size marker in nucleic acid or protein electrophoresis, chromatography, etc. Defined restriction fragments can be determined by scanning the sequence for restriction sites, calculating the size, and performing the corresponding restriction digest. A Chp cDNA as shown in FIG. 1 (SEQ ID NO: 1) can be used as a molecular weight marker in nucleic acid electrophoresis.

Another aspect of the present invention relates to the regulation of biological pathways in which a Chp gene is involved, particularly pathological conditions, including cancer, hyperproliferative diseases, tumors, neuron metabolism (e.g., neuronal transmission, axonal transport), cell-cycle diseases, reproductive diseases (e.g., involving production of sperm, eggs, fertility), response to cytokinins and growth factors, etc. In general, the present invention relates to methods of regulating a biological response in which Chp, or a homolog thereof, participates, e.g., by being a participant in the biochemical pathway which leads to the ultimate cellular response. For instance, an aspect of the invention relates to methods of modulating signal transduction in which Chp is involved. Since such signal transduction can lead to various biological responses, including transcriptional activation of certain genes. Thus, the invention relates to methods of controlling expression of these genes by modulating Chp activity. Any of the methods described in, e.g., U.S. Pat. Nos. 5,767, 075; 5,753,446; 5,728,536; 5,667,314; and 5,459,036 can be utilized in accordance with the present invention, e.g., using Chp, biologically-active fragments thereof, or a homologs thereof. Signal transduction mediated by Chp can be modulated by administering various agents, including antibodies to Chp, a dominant negative Chp gene (see, examples), PakR, etc.

The present invention also relates to methods of identifying compounds which modulate a PAK kinase stimulatory activity or a JNK kinase stimulatory activity of a mammalian Chp polypeptide, or a biologically-active fragment thereof, comprising the steps of, e.g., contacting, in the presence of a test compound, a Chp polypeptide, or an activated biologically-active polypeptide fragment thereof, with a JNK or PAK polypeptide, or a biologically-active fragment thereof, under conditions effective for the Chp polypeptide, or fragment thereof, to stimulate kinase activity of JNK or PAK; detecting the kinase activity; and identifying whether the test compound modulates the stimulatory activity of the Chp polypeptide by comparing the amount of kinase activity in the presence and absence of the test compound. These steps can be accomplished in any order; one or more of these steps can also be omitted if desired. Additional steps can also be utilized.

Detection of the kinase activity can be accomplished in any desired way. For example, JNK or PAK can be isolated after the step of contacting and measured for kinase activity. Isolation can be accomplished conventionally, e.g., using antibodies to JNK or PNK, or antibodies to polypeptide epitopes that are fused in-frame to JNK or PNK. Kinase assays can be carried at as described, e.g., in Bagrodia et al., *J. Biol. Chem.*, 270:27995-27998, 1995 or Coso et al., *Cell*, 81:1137-1146, 1995, using appropriate substrates, $^{32}$P-ATP, pH, buffers, etc. For PAK kinase assays, substrates can be, e.g., MBP. For JNK assays, substrates can be e.g., c-Jun, GST-c-Jun(79), GST-ATF2(96), etc. Detection can be accomplished in various ways, including autoradiography when using radioactive ATP.

The present invention also relates to a method of isolating a compound that modulates the binding between a mammalian Chp and a regulatory domain of PAK, or any other polypeptide which Chp normally binds or interacts. In one embodiment, compounds which modulate binding between Chp and a PakR regulatory domain are identified. One method involves the steps of: contacting a human Chp polypeptide, an activated form of Chp, or a biologically-active polypeptide fragment thereof (collectively, "polypeptides"), with a test compound under conditions effective for said compound to modulate binding between the Chp polypeptide said the PakR regulatory domain; and detecting binding between the Chp polypeptide and the PakR regulatory domain in the presence and absence of the test compound. These steps can be accomplished in any order; one or more of these steps can also be omitted if desired. Additional steps can also be utilized.

The test compound can be any agent suspected of modulating activity. For example, such compounds can include polypeptide derivatives or mimics of Chp which comprise a region of Chp which acts as an antagonist by interfering or competing with the normal interaction of Chp with the binding region of PakR or with effectors which are involved in such binding. Other agents included, e.g., naturally occurring compounds, chemicals synthesized by combinatorial chemistry, nucleic acids (such as aptamers), antisense, antibodies to regions of Chp, natural ligands which stimulate Chp, TPA and derivatives thereof, etc. In addition, GTP exchange factors (such as GEFs), GAPs, and other factors and polypeptides which regulate the G protein signaling family can be utilized as test compounds, such as p115 RhoGEF, Lsc, DRhoGEF2, fragments thereof, etc. See, e.g., Kozasa et al., *Science*, 280:2109-21111, 26 Jun. 1998.

In general, the methods, assays, tests can be conducted in environment in which the assay works for its intended purpose, i.e., to achieve and modulate kinase stimulation or to achieve and modulate binding. The test compound is preferably contacted with Chp polypeptides in a milieu in which kinase stimulation or binding can occur. The milieu can be in vitro or in vivo. Such a milieu includes effective conditions. These conditions can be determined in the absence of the test compound to establish a baseline activity, e.g., as in a control. The effective reaction conditions can be routinely selected, e.g., using appropriate salts, buffers, reducing and/or oxidizing agents, pH=s, etc.

By the term "modulate," it is meant that the stimulatory activity, is increased, enhanced, increased, agonized (acts as an agonist), promoted, decreased, reduced, blocked, or antagonized (acts as an agonist). Modulation can increase activity more than 1-fold, 2-fold, 3-fold, 10-fold, etc., over baseline values. Modulation can decrease its activity below baseline values.

The mammalian Chp polypeptide, or biologically-active polypeptide fragment thereof (collectively, "polypeptides") whose activity is to be modulated is preferably a rat polypeptide. The Chp polypeptide can have a naturally occurring sequence, e.g., as shown in FIG. 1 (SEQ ID NO: 1), an activated sequence (See above, "an activated form," e.g., where glycine 40 is substituted by valine), or other variants which possess kinase stimulatory or binding activity. The mammalian Chp can also comprise one or more of its aforementioned domains alone, or in combination with regions from other proteins. An inactive Chp polypeptide (e.g., see description of the dominant, negative allele) can also be identified, where an objective is to identify compounds which restore its activity.

The methods can be accomplished using mixtures in which each component is added to a test, in cell lysates, in whole cells, or combinations thereof. For instance, the kinase stimulatory activity or binding activity can measured in a reaction mixture where a Chp polypeptide, JNK or PAK polypeptides, and other components are combined to form a reaction mixture. In this method, the Chp polypeptide can be added, e.g., substantially purified, as a component of a cell, or as a soluble extract. In each case, the Chp polypeptide can be obtained from a natural source, a recombinant source (i.e., a Arecombinant≡polypeptide is a produced by genetic engineering, e.g., introduced into a cell line on a plasmid, vector, naked DNA, etc., and expressed in the cell), or it can be produced. The Chp polypeptide can be expressed in a mammalian cell, an insect cell line, or in bacteria, e.g., as a fusion or non-fusion protein.

Preferably, Chp is expressed in a cell line transformed with a Chp coding sequence (e.g., a cDNA, a gene, a genomic fragment, etc.). In the latter case, the Chp is present as a heterologous component of the cell; by heterologous, it is meant that the Chp is coded for by a coding sequence that has been introduced by the hand of a person into the cell, e.g., by transfection, transformation, etc. Preferably, the Chp is expressed at high levels in the cell (bacterial, yeast, insect, mammalian, etc.). Any cell line can be used, including cell lines which are normal, mutant, temperature-sensitive mutant, etc. A rat Chp is a preferred coding sequence. See, e.g., FIG. 1 (SEQ ID NO:1).

In a preferred embodiment, the kinase stimulatory activity is measured in whole cells, e.g., as described in the examples. In this method, Chp and PAK or JNK are introduced into a desired cell (such as a yeast cell) by transfection of nucleic acid coding sequences which are expressible in such cell. The coding sequences can be operably linked to any desired promoter that is functional within the cell, including inducible and constitutive promoters. The PAK and JNK polypeptides preferably comprise a "tag" which acts as a handle, permitting the polypeptides to be retrieved for kinase assay, after their expression in the cells and stimulation by Chp. The "tag" is typically a polypeptide sequence, such as myc or hemagluttinin to which an antibody has been produced. Thus, the "tag" can be a polypeptide epitope, i.e., any polypeptide sequence to which antibodies can generated. As mentioned, wild-type, activated, or biologically-active fragments thereof, of Chp can be used. Once the cells are transfected with the coding sequences, and incubated for a desired time under appropriate conditions, the cells can be lysed and assayed for kinase activity. The "tag" facilitates retrieval of JNK or PNK by immunoprecipitation for kinase assay. Kinase assay can also be performed on whole cells using in situ techniques. A test compound can be added to the cells at any time, including before transfection, after transfection, after transfection and induction of the promoters, etc.

As discussed, the binding method can be accomplished in any desired way, including as a competition assay using a labeled binding ligand, such as PakR, in either solid or liquid phase. In a preferred embodiment, the method of identifying compounds which modulate binding to Chp can be performed in whole cells. By way of illustration, in the examples, a temperature sensitive yeast cell line, e.g., cdc25-2, is utilized which is unable to survive at a restrictive temperature. Recruitment of Ras to the plasma membrane results in the rescue of the lethal phenotype. To take advantage of this, a Chp polypeptide can be constructed which contains an in-frame plasma membrane targeting sequence, such as a v-src myristolation sequences. Transformation of the cell line with a Chp polypeptide containing the plasma membrane targeting sequence and a fusion protein containing Ras and a domain capable of binding to Chp, rescues the temperature-sensitive defect. The Chp fusion polypeptide captures the Ras fusion protein, enabling it to reach the plasma membrane. Thus, by growing the cell line at the restrictive temperature, only those cells in which Chp binds to the Ras fusion protein can survive. The Ras fusion protein can comprise, in addition to a biologically-active part of Ras, any polypeptide having the ability to bind to Chp, such as PakR, such as PakR-Ras(61)deltaF ("bait"). In accordance with the method, the cells can be transformed with nucleic acids coding for the Chp membrane-targeted polypeptide and the bait. A test compound can be added to the cell at any time. If the compound interferes with the interaction between Chp and its ligand, e.g., PakR, the cell will not survive. In this manner, antagonists, and other compounds which reduce, decrease, etc., binding can be identified. The method can also be utilized to identify compounds which regulate binding by performing the experiments using a range of concentrations of the test compound and calculating and an $LD_{50}$. The latter permits the identification of compounds which either enhance or reduce binding between Chp and its binding ligand (the bait).

The present invention also relates to a method of identifying compounds which modulate a cytoskeletal-reorganizing activity of a Chp polypeptide, or a biologically-active polypeptide fragment thereof. In one embodiment of this method, a Chp polypeptide, or a biologically-active polypeptide fragment thereof, is introduced into a cell, which polypeptide is effective to stimulate reorganization of the cell's cytoskeleton. The method involves, e.g., contacting the cell with a test compound under conditions effective for the compound to modulate the polypeptides effect in stimulating reorganization of said cell's cytoskeleton. The effect on the cytoskeleton can be detecting in various ways, including by visualization using an agent which binds to actin or other elements (such as vinculin) of the cytoskeleton. Such agents, include, detectably labeled phalloidin (e.g., rhodamine, fluorescein), antibodies to actin or vinculin, or by antibodies which recognize Chp or a part of it (e.g., in the examples, it is fused with a polypeptide which can be detected using an antibody). The cytoskeleton can be visualized in the presence and absence of the test compound. See, e.g., Symons et al., *Cell,* 84: 723-734, 1996; Nobes and Hall, *Cell,* 81: 53-62, 1995.

Another way in which Chp function can be modulated is by regulating a pathway involved in its expression, e.g., modulating its transcription, mRNA stability, translation, post-translational modifications, processing (such as cleavage at the internal cleavage site), etc. Expression can be regulated using different agents, e.g., an anti-sense nucleic acid, a ribozyme, an aptamer, a synthetic compound, or a naturally-occurring compound.

The present invention also relates to methods of identifying genes whose transcription is modulated by Chp. For example, activated Chp can be introduced into cells and their expression/transcription patterns can be analyzed in the presence and absence of Chp. Expression analysis can be performed conventionally. For example, high-density oligonucleotide chip arrays can be designed to monitor expression. Such chips can contain all or subsets of the human genome. See, e.g., Anderson et al., Topics in Current Chemistry, Vol. 194, pages 117-129, 1998. Southern, Current Biology, 7:85-88, 1996; Marshall and Hodgson, Nature Biotechnology, 16:27-31, 1998.

The present invention also relates to a method of identifying natural ligands and signals which modulate Chp. For instance, cells expressing Chp can be contacted with various cellular products and then assayed for activation of the signal pathway in which Chp is involved. In one embodiment, heterologous Chp is expressed in a cell; such cell is contacted with cells, or products thereof, which have been transformed with a cDNA library. Chp activation is measured routinely as described herein (e.g., by kinase activity, cytoskeletal rearrangement, etc). If a transformed cell, or product thereof, results in Chp activation, the cDNA expressed in such transformed cell is then isolated and identified.

Compounds identified in any of the aforementioned assays can be useful to modulate Chp activity in a cell, a tissue, a whole organism, in situ, in vitro (test tube, a solid support, etc.), in vivo, or in any desired environment. In general, a compound having such an in vitro activity will be useful in vivo to modulate a biological pathway associated with Chp, e.g., cell cycle disorders, stress responses, apoptosis, mitogenesis, differentiation, yeast infections (e.g., when modulating a yeast Chp homolog), fertility diseases, neurological disorders, cancer, metastasis, tumorogenesis, etc.

To treat a disease, the compound, or mixture, can be formulated into a pharmaceutical composition comprising a pharmaceutically acceptable carrier and other excipients as apparent to the skilled worker. See, e.g., *Remington's Pharmaceutical Sciences*, Eighteenth Edition, Mack Publishing Company, 1990. Such composition can additionally contain effective amounts of other compounds.

The present invention also relates to antibodies which specifically recognize Chp. An antibody specific for Chp means that the antibody recognizes a defined sequence of amino acids within or including a Chp, e.g., the rat sequence of FIG. 1 (SEQ ID NO:2). Thus, a specific antibody will generally bind with higher affinity to an amino acid sequence, i.e., an epitope, found in FIG. 1 (SEQ ID NO:2) than to a different epitope(s), e.g., as detected and/or measured by an immunoblot assay or other conventional immunoassay. Thus, an antibody which is specific for an epitope of rat Chp is useful to detect the presence of the epitope in a sample, e.g., a sample of tissue containing rat Chp gene product, distinguishing it from samples in which the epitope is absent. Such antibodies are useful as described in Santa Cruz Biotechnology, Inc., Research Product Catalog, and can be formulated accordingly, e.g., 100 µg/ml. Antibodies, e.g., polyclonal, monoclonal, recombinant, chimeric, humanized, can be prepared according to any desired method. See, also, screening recombinant immunoglobulin libraries (Orlandi et al., *Proc. Natl. Acad. Sci.*, 86: 3833-3837, 1989; Huse et al., *Science*, 256: 1275-1281, 1989); in vitro stimulation of lymphocyte populations; Winter and Milstein, *Nature*, 349: 293-299, 1991. For example, for the production of monoclonal antibodies, a polypeptide according to FIG. 1 (SEQ ID NO:2) can be administered to mice, goats, or rabbit subcutaneously and/or intraperitoneally, with or without adjuvant, in an amount effective to elicit an immune response. The antibodies can also be single chain or FAb fragments. The antibodies can be IgG, subtypes, IgG2a, IgG1, etc. Antibodies, and immune responses, can also be generated by administering naked DNA See, e.g., U.S. Pat. Nos. 5,703,055; 5,589,466; 5,580,859.

Chp, or fragments thereof, for use in the induction of antibodies do not need to have biological activity; however, they must have immunogenic activity, either alone or in combination with a carrier. Peptides for use in the induction of Chp-specific antibodies may have an amino sequence consisting of at least five amino acids, preferably at least 10 amino acids. Short stretches of Chp amino acids, e.g., five amino acids, can be fused with those of another protein such as keyhole limpet hemocyanin, or another useful carrier, and the chimeric molecule used for antibody production.

Several different approaches, as mentioned, can be utilized to prepare antibodies specific for Chp. For instance, in one approach, denatured Chp from purified Chp (e.g., purified by reverse-phase HPLC separation) is obtained in quantities up to 75 mg. This denatured protein can be used to immunize mice or rabbits using standard protocols; about 100 micrograms are adequate for immunization of a mouse, while up to 1 mg might be used to immunize a rabbit. For identifying mouse hybridomas, the denatured protein can be radioiodinated and used to screen potential murine B-cell hybridomas for those which produce antibody. This procedure requires only small quantities of protein, such that 20 mg would be sufficient for labeling and screening of several thousand clones.

In another approach, an amino acid sequence of Chp, as deduced from the cDNA, is analyzed to determine regions of high immunogenicity. Polypeptides comprising these regions are synthesized and used in suitable immunization protocols to raise antibodies. Analysis to select appropriate epitopes is described by Ausubel F M et al (1989, *Current Protocols in Molecular Biology*, Vol 2. John Wiley & Sons). The optimal amino acid sequences for immunization are usually at the C-terminus, the N-terminus and those intervening, hydrophilic regions of the polypeptide which are likely to be exposed to the external environment when the protein is in its natural conformation. Typically, selected peptides, about 15 residues in length, are synthesized using an Applied Biosystems Peptide Synthesizer Model 431A using fmoc-chemistry and coupled to keyhole limpet hemocyanin (KLH, Sigma) by reaction with M-maleimidobenzoyl-N-hydroxysuccinimide ester (MBS; cf. Ausubel F M et al, supra). If necessary, a cysteine may be introduced at the N-terminus of the peptide to permit coupling to KLH. Rabbits are immunized with the peptide-KLH complex in complete Freund's adjuvant. The resulting antisera are tested for antipeptide activity by binding the peptide to plastic, blocking with 1% BSA, reacting with antisera, washing and reacting with labeled (radioactive or fluorescent), affinity purified, specific goat anti-rabbit IgG.

Hybridomas can also be prepared and screened using standard techniques. Hybridomas of interest are detected by screening with labeled Chp to identify those fusions producing the monoclonal antibody with the desired specificity. In a typical protocol, wells of plates (FAST, Becton-Dickinson, Palo Alto, Calif.) are coated with affinity purified, specific rabbit-anti-mouse (or suitable anti-species Ig) antibodies at 10 mg/ml. The coated wells are blocked with 1% BSA, washed and exposed to supernatants from hybridomas. After incubation the wells are exposed to labeled Chp, 1 mg/ml. Clones producing antibodies will bind a quantity of labeled Chp which is detectable above background. Such clones are expanded and subjected to 2 cycles of cloning at limiting dilution (1 cell/3 wells). Cloned hybridomas are injected into pristine mice to produce ascites, and monoclonal antibody is purified from mouse ascitic fluid by affinity chromatography on Protein A. Monoclonal antibodies with affinities of at least $10^8$ M, preferably $10^9$ to $10^{10}$, or stronger, will typically be made by standard procedures as described in Harlow and Lane (1988) *Antibodies: A Laboratory Manual*. Cold Spring Harbor Laboratory, or Goding (1986) *Monoclonal Antibodies: Principles* and Practice, $2^{nd}$ Ed. Academic Press N.Y.

Useful sequences for generating antibodies, include, KLNAKGVRTLSRCRWKK at amino acids 215-231 of FIG. 1 (SEQ ID NO:9), RELSEAEPPPLPASTPPPRRRSAP-PELG at amino acids 4-31 of FIG. 1 (SEQ ID NO:12), and fragments thereof.

Particular Chp antibodies are useful for the diagnosis of prepathologic conditions, and chronic or acute diseases which are characterized by differences in the amount or distribution of Chp. Diagnostic tests for Chp include methods utilizing the antibody and a label to detect Chp in human (or mouse, etc, if using mouse, etc.) body fluids, tissues or extracts of such tissues.

The polypeptides and antibodies of the present invention may be used with or without modification. Frequently, the polypeptides and antibodies will be labeled by joining them, either covalently or noncovalently, with a substance which provides for a detectable signal. A wide variety of labels and conjugation techniques are known and have been reported extensively in both the scientific and patent literature. Suitable labels include radionuclides, enzymes, substrates, cofactors, inhibitors, fluorescent agents, chemiluminescent agents, magnetic particles and the like. Patents teaching the use of such labels include U.S. Pat. Nos. 3,817,837; 3,850,752; 3,939,350; 3,996,345; 4,277,437; 4,275,149; and 4,366,241. Also, recombinant immunoglobulins may be produced as shown in U.S. Pat. No. 4,816,567, incorporated herein by reference.

A variety of protocols for measuring soluble or membrane-bound Chp, using either polyclonal or monoclonal antibodies specific for Chp are known in the art. Examples include enzyme-linked immunosorbent assay (ELISA), radioimmunoassay (RIA) and fluorescent activated cell sorting (FACS). A two-site monoclonal-based immunoassay utilizing monoclonal antibodies reactive to two non-interfering epitopes on EC is preferred, but a competitive binding assay may be employed. These assays are described, among other places, in Maddox, Del. et al (1983) *J Exp Med* 158: 1211.

Antibodies and other ligands which bind Chp can be used in various ways, including as therapeutic, diagnostic, and commercial research tools, e.g., to quantitate the levels of Chp polypeptide in animals, tissues, cells, etc., to identify the cellular localization and/or distribution of it, to purify it, or a polypeptide comprising a part of it, to modulate the function of it, in Western blots, ELIZA, immunoprecipitation, RIA, etc. The present invention relates to such assays, compositions and kits for performing them, etc. Utilizing these and other methods, an antibody according to the present invention can be used to detect Chp polypeptide or fragments thereof in various samples, including tissue, cells, body fluid, blood, urine, cerebrospinal fluid. A method of the present invention comprises: a) contacting a ligand which binds to a peptide of FIG. 1 (SEQ ID NO: 2) under conditions effective, as known in the art, to achieve binding, and b) detecting specific binding between the ligand and peptide. By specific binding, it is meant that the ligand attaches to a defined sequence of amino acids, e.g., within or including the amino acid sequence of FIG. 1 (SEQ ID NO: 2) or derivatives thereof.

Native or recombinant Chp can be purified by immunoaffinity chromatography using Chp-specific antibodies. In general, an immunoaffinity column is constructed by covalently coupling the anti-Chp antibody to an activated chromatographic resin.

Polyclonal immunoglobulins are prepared from immune sera either by precipitation with ammonium sulfate or by purification on immobilized Protein A (Pharmacia LKB Biotechnology, Piscataway, N.J.). Likewise, monoclonal antibodies are prepared from mouse ascites fluid by ammonium sulfate precipitation or chromatography on immobilized Protein A. Partially purified Ig is covalently attached to a chromatographic resin such as CnBr activated Sepharose (Pharmacia LKB Biotechnology, Piscataway, N.J.). The antibody is coupled to the resin, the resin is blocked, and the derivative resin is washed according to the manufacturer's instructions.

An immunoaffinity column is utilized in the purification of Chp by preparing a fraction from cells containing Chp. This preparation can be derived by solubilization of the whole cell or of a subcellular fraction obtained via differential centrifugation by the addition of detergent or by other methods well known in the art. Alternatively, soluble Chp containing a signal sequence may be secreted in useful quantity into the medium in which the cells are grown.

A soluble Chp-containing preparation is passed over the immunoaffinity column, and the column is washed under conditions, e.g., high ionic strength buffers in the presence of detergent, that allow the preferential absorbance of Chp. Then, the column is eluted under conditions that disrupt antibody/Chp binding (e.g., a buffer of pH 2-3 or a high concentration of a chaotrope such as urea or thiocyanate ion), and the Chp is collected.

In addition, ligands which bind to a Chp polypeptide according to the present invention, or a derivative thereof, can also be prepared, e.g., using synthetic peptide libraries or aptamers (e.g., Pitrung et al., U.S. Pat. No. 5,143,854; Geysen et al., 1987, *J. Immunol. Methods*, 102:259-274; Scott et al., 1990, *Science*, 249:386; Blackwell et al., 1990, *Science*, 250: 1104; Tuerk et al., 1990, *Science*, 249: 505.)

The antibodies or derivatives thereof can also be used to inhibit expression of Chp or a fragment thereof. The levels of Chp polypeptide can be determined alone or in combination with other gene products. In particular, the amount (e.g., its expression level) of Chp polypeptide can be compared (e.g., as a ratio) to the amounts of other polypeptides in the same or different sample, e.g., actin. In general, reagents which are specific for Chp can be used in diagnostic and/or forensic studies according to any desired method, e.g., as U.S. Pat. Nos. 5,397,712; 5,434,050; 5,429,947.

The present invention also relates to a Chp polypeptide, prepared according to a desired method, e.g., as disclosed in U.S. Pat. No. 5,434,050. A labeled polypeptide can be used, e.g., in binding assays, such as to identify substances that bind or attach to Chp, to track the movement of Chp in a cell, in an in vitro, in vivo, or in situ system, etc.

A nucleic acid, polypeptide, antibody, Chp, ligand etc., according to the present invention can be isolated. The term "isolated" means that the material is in a form in which it is not found in its original environment, e.g., more concentrated, more purified, separated from component, etc. An isolated nucleic acid includes, e.g., a nucleic acid having the sequence of Chp separated from the chromosomal DNA found in a living animal. This nucleic acid can be part of a vector or inserted into a chromosome (by specific gene-targeting or by random integration at a position other than its normal position) and still be isolated in that it is not in a form which it is found in its natural environment. A nucleic acid or polypeptide of the present invention can also be substantially purified. By substantially purified, it is meant that nucleic acid or polypeptide is separated and is essentially free from other nucleic acids or polypeptides, i.e., the nucleic acid or polypeptide is the primary and active constituent.

The present invention also relates to a transgenic animal, e.g., a non-human-mammal, such as a mouse, comprising a Chp. Transgenic animals can be prepared according to known methods, including, e.g., by pronuclear injection of recombinant genes into pronuclei of 1-cell embryos, incorporating an artificial yeast chromosome into embryonic stem cells, gene targeting methods, embryonic stem cell methodology. See, e.g., U.S. Pat. Nos. 4,736,866; 4,873,191; 4,873,316; 5,082, 779; 5,304,489; 5,174,986; 5,175,384; 5,175,385; 5,221,778; Gordon et al., *Proc. Natl. Acad. Sci.*, 77:7380-7384 (1980); Palmiter et al., *Cell*, 41:343-345 (1985); Palmiter et al., *Ann. Rev. Genet.*, 20:465-499 (1986); Askew et al., *Mol. Cell. Bio.*, 13:4115-4124, 1993; Games et al. *Nature*, 373:523-527, 1995; Valancius and Smithies, *Mol. Cell. Bio.*, 11:1402-1408, 1991; Stacey et al., *Mol. Cell. Bio.*, 14:1009-1016, 1994; Hasty et al., *Nature*, 350:243-246, 1995; Rubinstein et al., *Nucl. Acid Res.*, 21:2613-2617,1993. A nucleic acid according to the present invention can be introduced into any non-human mammal, including a mouse (Hogan et al., 1986, in *Manipulating the Mouse Embryo: A Laboratory Manual*, Cold Spring Harbor Laboratory, Cold Spring Harbor, N.Y.), pig (Hammer et al., *Nature*, 315:343-345, 1985), sheep (Hammer et al., *Nature*, 315:343-345, 1985), cattle, rat, or primate. See also, e.g., Church, 1987, *Trends in Biotech.* 5:13-19; Clark et al., 1987, *Trends in Biotech.* 5:20-24; and DePamphilis et al., 1988, *BioTechniques*, 6:662-680. In addition, e.g., custom transgenic rat and mouse production is commercially available. These transgenic animals can useful animals models to test for Chp function, as food for a snake, as a genetic marker to detect strain origin (i.e., where a Chp or fragment thereof has been inserted), etc. Such transgenic animals can further comprise other transgenes. Transgenic animals (such as Chp knockouts) can be prepared and used according to U.S. application Ser. Nos. 08/866,058 and 09/000,846. A transgenic animal containing a Chp mutant (e.g., an activated Chp) or a Chp knockout can be combined with other gene mutations, e.g., knockouts or mutations in genes involved in the same or similar signaling pathway. Such genes include: Ras, Cdc42Hs, Racs, Rhos, PAKS, JNK, Jun, WASP, IQGAP, POSH, POR1, p67-phox, MLK3, MAP kinases, NCK, SOS, ERKs, p38, GEFs, GAPs, GDIs, Wiskott-Aldrich Syndrome protein, FTases, STE14, p53, Rb, Mtase, GTPases subunits, Dbl, Ibc, Ost, Lsc, and any genes mentioned above, below, or in the references incorporated herein, etc. Animals can be homozygous or heterozygous, depending on the desired use and phenotype.

Generally, the nucleic acids, polypeptides, antibodies, etc. of the present invention can be prepared and used as described in, U.S. Pat. Nos. 5,501,969, 5,506,133, 5,441,870; WO 90/00607; WO 91/15582;

For other aspects of the nucleic acids, polypeptides, antibodies, etc., reference is made to standard textbooks of molecular biology, protein science, and immunology. See, e.g., Davis et al. (1986), *Basic Methods in Molecular Biology*, Elsevir Sciences Publishing, Inc., New York; Hames et al. (1985), *Nucleic Acid Hybridization*, IL Press; Sambrook et al. (1989) *Molecular Cloning; Current Protocols in Molecular Biology*, Edited by F. M. Ausubel et al., John Wiley & Sons, Inc; *Current Protocols in Human Genetics*, Edited by Nicholas C. Dracopoli et al., John Wiley & Sons, Inc.; *Current Protocols in Protein Science*; Edited by John E. Coligan et al., John Wiley & Sons, Inc.; *Current Protocols in Immunology*; Edited by John E. Coligan et al., John Wiley & Sons, Inc.

EXAMPLES

Isolation of a novel Cdc42Hs homologue protein (Chp) that interacts specifically with PAK. To identify proteins that interact with PAK65 we used a modified form of the Sos recruitment system (SRS) (Aronheim et al., Mol Cell Biol 1997, 17: 3094-3102). This novel two hybrid system aims to detect protein-protein interactions within the inner surface of the plasma membrane. The SRS system is based on the finding which demonstrated that targeting the Ras exchange factor Sos to the plasma membrane was sufficient to rescue the temperature sensitive cdc25 allele in yeast. Using this finding to our advantage, we constructed a novel two hybrid yeast screen by transforming a membrane targeted mammalian cDNA library into a cdc25-2 temperature sensitive yeast strain together with bait fused to Ras (Aronheim et al., Mol Cell Biol 1997, 17: 3094-3102). An interaction between the bait and a protein displayed on the membrane will lead to the recruitment of Ras to the plasma membrane and consequently to the gain of cell.

PAK2 regulatory domain (PakR) was fused at the N-terminus of RasL61 lacking the CAAX box and was subcloned into pADNS plasmid designated, PakR-Ras(61)ΔF. Rat pituitary cDNA library was constructed into pYES vector containing the v-src myristolation sequence as previously described (Aronheim et al., Mol Cell Biol 1997, 17: 3094-3102). Expression of the library was put under the control of GAL1, galactose inducible promoter. Cells were transformed with the library and PakR-Ras(61)ΔF-fusion and approximately $0.5 \times 10^6$ transformants were grown on 24° C. for four days and subsequently plated onto galactose plates at 36° C. Five clones that were shown to grow in a galactose dependent manner were isolated and subsequently the specificity of the interaction was examined. Clone numbers 1, 2, 5 and 6 were able to grow at 36° C. only when cotransformed with PakR-Ras(61)ΔF bait and not with a non relevant bait Ras(61)ΔF-JDP2, suggesting that the interaction is dependent on the bait PAK65. In contrast, clone number 8 grew at 36° C. when it was cotransformed with both baits. Subsequently, the nucleotide sequence revealed that clone #8 is a homolog of Sos which by itself when targeted to the membrane is able to activate the yeast Ras and confer growth at the restrictive temperature. Clones 1, 2 and 5 were identical and exhibited sequence homology to the GTPase Cdc42Hs and Rac1. Since this cDNA appeared independently three times in our screen, we focused further analysis on this clone. The characterization of clone 6 will be described elsewhere. The clone reveals ~52% sequence identity to Cdc42Hs and therefore was designated Cdc42Hs Homologue Protein-Chp and encodes a protein of ~36 Kda. Interestingly, in addition to the homology to Cdc42Hs, Chp contains sequences at the N and C termini that are not related to Cdc42Hs. An additional 28 amino acids were found at the N-terminus of Chp that are absent in Cdc42Hs. This additional sequence contains polyproline typical of SH3 binding regions. The C-terminus of Chp does not contain the classical CAAX box that is conserved among all Ras related GTPases (Didsbury et al., J. Biol Chem 1989, 264: 16378-16382). The CAAX domain is responsible for lipid modification and membrane attachment of all small GTPase from the Rho family. Instead, Chp contains additional 32 amino acids that do not share any sequence homology to known proteins in the data base.

Chp transcription To determine the tissue distribution of Chp we used a specific probe corresponding to the GTPase domain of Chp corresponding to amino acids 102-151 to hybridize multiple Rat tissues mRNAs using Northern blot analysis (Clontech). This region exhibits only 62% identity with other members of the family. A single mRNA species of about 1.5 Kb was detected in high levels in brain and testes, whereas, lower amounts were also detected in spleen and lung tissues. Interestingly, small size mRNA (1.0 and 1.4) were reported for Rae related proteins (Didsbury et al., J. Biol Chem 1989, 264: 16378-16382). Hybridization with probes corresponding to the C and N terminal as well as Chp full length resulted similar results.

Chp expression To determine the size of Chp and to identify the expression of Chp in 293 cell line, polyclonal antibodies were generated against a peptide corresponding to a unique region of Chp located at the C-terminal (amino acids 216 KLNAKGVRTLSRCRWKK 232; SEQ ID NO:13). To compare the size of endogenous Chp with the cloned cDNA we fused Chp cDNA to a myc epitope tag sequences and used this plasmid to overexpress Chp in 293 cells. Whole cell extracts derived from either transfected or non-transfected 293 cells were separated on SDS-PAGE and subjected to Western blotting with anti-myc antibodies, subsequently, the nitrocellulose filter was incubated with affinity purified anti-Chp antibodies. The results indicate that the size of the transfected Chp was identical to the protein detected in non transfected 293 cell line using the anti-Chp antibody.

PAK interacts with the activated Chp mutant. Pak regulatory domain (PakR) interacts with the activated forms of Rac and Cdc42. We sought to test the binding of PakR to Chp. Based on the sequence homology to Cdc42 and other Rho GTPases we generated various Chp mutants that are expected to differ in their GDP/GTP bound state. To make a constitutively active Chp, we substituted glycine 40 with valine (SEQ ID NO:10). Substitution of the equivalent amino acid at position 12 in Rac and Cdc42Hs (G12V) results in an active allele that is defective in GTPase hydrolysis. In addition, we mutated the equivalent position on Chp and substituted amino acid 45 to asparagine (SEQ ID NO:11). Substitution of the corresponding amino acid at position 17 to asparagine in other Rho GTPases results in a dominant negative allele that is locked in the GDP bound inactive form (Erickson et al., J Biol Chem 1996, 271: 26850-26854). A cdc25-2 yeast strain was cotransfected with plasmids encoding for different Chp mutants fused to myristoylation sequences together with PakR-Ras(61)ΔF bait. A constitutively active (Chp Ac.) and WT Chp interacted with PakR and not with the dominant negative form of Chp. Similarly, constitutively active and WT Cdc42Hs interacted with PakR but not with the dominant negative form. Interestingly, under the same assay conditions, only the activated mutant Rac1 interacted with PakR and not the wild type or the dominant negative RacN17. This data suggests that the specific interaction between Chp and PakR is dependent on the activation state of the GTPase. The reason for the interaction of the WT forms of Chp and Cdc42Hs but not of Rac1, is may be due to the different sensitivity of these GTPases to the yeast nucleotide exchange factor Cdc24. Interaction of Cdc42Hs and Chp with the putative exchange factor will subsequently will load the GTPase with GTP and thereby generate active forms of Cdc42Hs and Chp.

The role of Chp C-terminal region for Pak65 binding. In order to investigate the role of Chp amino and carboxy terminal sequences, we further mutated Chp Ac. by deletion of either the C or N terminal, or both. Chp mutants were transformed into cdc25-2 yeast strain together with the PakR bait. Chp devoid of its C-terminal domain was unable to bind PakR, whereas deletion of the N-terminal had no significant effect on PakR binding. This result suggests that the extended C-terminal is either involved directly in binding PakR or the loss of this domain results in a conformational change in Chp that prevents PakR binding.

Chp selectively activates the JNK MAP kinase pathway We and others have shown that the constitutively active forms of Cdc42HsV12 and RacV12 stimulate the JNK and p38 MAP kinase cascade (Minden et al., Cell 1995, 81: 1147-1157 and Coso et al., Cell 1995, 81: 1137-1146). To test if Chp has a similar effect on JNK cascade, we co-transfected 293 cells with various forms of Chp together with expression vectors encoding for hemagglutinin epitope (HA) tagged of either: JNK2, ERK2 or p38. JNK, ERK and p38 were immunoprecipitated from transfected cell extracts followed by in-vitro kinase assay using conventional substrates. Both wild type and activated forms of Chp stimulated the JNK kinase. In contrast, the dominant negative form of Chp did not activate the JNK pathway in Hela cells. As described for Cdc42 and Rac GTPases, Chp did not significantly activate the ERK2. In addition, surprisingly, Chp did not induce the activation of the p38 kinase. This data suggests that Chp, in contrast to Rac and Cdc42Hs, is a selective activator for the JNK-MAP kinase cascade and not for the ERK or p38 pathways.

Chp is co-localized with b-COP at the Golgi apparatus To determine the cellular localization of Chp, we microinjected a Myc tagged Chp in mammalian expression vector into PAE cells and visualized Chp expression by staining the cells with anti myc antibody. Chp was concentrated exclusively in close proximity to the nucleus in an area that resembles the Golgi apparatus. Co-staining of injected cells with an antibody that recognizes the Golgi protein b-COP confers that Chp is colocalized with the coatomer protein b-COP at the Golgi. Interestingly, endogenous Cdc42Hs was recently was shown to co-localize with b-COP at the Golgi apparatus (Erickson, et al., J Biol Chem 1996, 271: 26850-26854).

Chp is implicated in the induction of lamellipodia To test whether Chp plays a role in the control of the actin cytoskeleton, we microinjected plasmids encoding for activated Chp mutants and stained for either Chp expression or polymerized actin. Chp was concentrated in one side around the nucleus at the Golgi apparatus and injected cells exhibited morphological changes demonstrated by induction of lammelipodia. In addition, lack of stress fibers was seen in Chp injected cells. Further work is required to fully characterize the specific morphological changes that are mediated by various Chp mutants.

Material and Methods:

Plasmids and Constructs:

Chp expression vectors: mammalian expression were generated by fusion of Chp cDNA in frame with myc epitope tag into pCan mammalian expression vector. Yeast expression vectors were generated by fusion Chp cDNA in frame with Src myristoylation signal into pYes2 expression vector (Invitrogen Inc.). Plasmids encoding for different Cdc42 mutants were subcloned into pYes2 expression vector using regular procedure.

Chp mutagenesis: Chp mutagenesis was performed using the Chameleon mutagenesis kit (Stratagene Inc.) according to the manufacturer instructions.

Northern blot analysis: Northern blot were purchased from Clontech Inc. and performed as described in the manufacturer protocols. The specific probes were generated by random primer labeling kit (Stratagene Inc.). Probes were incubated with filters for 2 hours at 68° C. The filters were washed three times with 2×SSC containing 0.1% SDS at room temperature followed by two washes with 0.1×SSC containing 0.1% SDS at 55° C.

Western blot analysis: protein extracts (50 ug/lane) were resolved on a sodium dodecyl sulfate (SDS)-12.5% polyacrylamide gel, blotted onto nitrocellulose membrane probed with anti myc antibodies or affinity purified Chp antibodies. Anti mouse antibody or protein-A conjugated to horseradish peroxidase were used in a secondary incubation. The nitrocellulose blots were developed using SuperSignal chemiluminescent reaction kit (Promega Inc.). Chp antibody was generated against the C-terminus peptide 215 KLNAKGVRTLSRCRWKK 231 (SEQ ID NO:9) conjugated to KLH. Antibody purification was carried out by coupling 10 mg of the peptide to 10 ml of agarose gel. The gel was equilibrated with PBS and the crude serum was applied to the gel, washed and antibody was eluted by glycin buffer pH 2.0.

Yeast manipulations: Conventional yeast transfection and manipulation protocols were used as described (Aronheim et al., Mol Cel Biol 1997, 17: 3094-3102).

Transfection and In vitro kinase assays: 293 cells were transfected by the CaPo4 precipitation procedure. Cells were cotransfected with pCan expression plasmids driving the expression of different Chp mutants (5 ug) with Sr-alpha expression vector driving the expression of the different HA epitope tagged kinases (5 ug). 48 hours following transfection, protein was extracted and in vitro kinase assays were performed as described (Hibi et al., Genes Dev 1993, 17: 2135-2148). The following plasmids used for HA-ERK2, HA-JNK2 and HA-p38 and the following purified substrates (5 ug/assay) were used respectively: myelin basic protein (MBP), GST-c-Jun 1-79, GST-ATF2D.

Microinjections and Immunofluorescence Microscopy

PAE cells were grown in DMEM medium containing 10% fetal bovine serum and were plated on coverslip. Expression vectors encoding Chp diluted to a concentration of 50 ng/ul in injection buffer (5 mM glutamate, 130 mM KCL), were microinjected into the nucleus of ~100 of sub-confluent PAE cells. Injected cells were incubated for 16-20 hr. at 37° C. and fixed in 4% formaldehyde. Cells were permeabilized with PBS containing 0.1% TritonX-100 and incubated in the presence of the primary monoclonal antibodies anti Myc or anti b-COP (a gift from Dr. Richard Khan) for 60 min. The coverslips were washed with PBS containing 0.1% TritonX-100 and were incubated for 30 min. with the second antibody Texas Red conjugated anti mouse antibody. To visualize F-actin, cells were washed again and were incubated with FITC conjugated phalloidin. Fluorescence photomicroscopy was carried out on a Zeiss Axiophot with appropriate filters for fluorescence detection.

What is claimed:

1. An isolated full-length Chp polypeptide, or a polypeptide fragment thereof, wherein (i) said Chp polypeptide or polypeptide fragment thereof has about 95% or greater identity to the amino acid sequence presented as SEQ ID NO:2, and (ii) said Chp polypeptide or polypeptide fragment thereof has at least one biological activity selected from the group consisting of a PAK regulatory domain binding activity, a PAK kinase stimulatory activity, a JNK kinase stimulatory activity, a cytoskeletal-reorganizing activity, a Chp-specific immunogenic activity directed to SEQ ID NO:2, and combinations thereof.

2. The isolated Chp polypeptide or polypeptide fragment of claim 1, comprising the amino acid sequence presented as SEQ ID NO:2.

3. The isolated Chp polypeptide or polypeptide fragment of claim 1, wherein said Chp polypeptide or polypeptide fragment thereof has about 98% or greater identity to the amino acid sequence presented as SEQ ID NO:2.

4. The isolated Chp polypeptide or polypeptide fragment of claim 1, wherein said fragment comprises at least one polypeptide having a sequence selected from the group consisting of SEQ ID NO: 6, SEQ ID NO:7, SEQ ID NO:8, SEQ ID NO:9, SEQ ID NO:12, and SEQ ID NO:13.

5. The isolated Chp polypeptide or polypeptide fragment of claim 1, wherein said fragment is a Chp polypeptide fragment consisting essentially of a polypeptide having a sequence selected from the group consisting of SEQ ID NO: 6, SEQ ID NO:7, SEQ ID NO:8, SEQ ID NO:9, SEQ ID NO:12, and SEQ ID NO:13.

6. A chimeric polypeptide comprising, a full-length Chp polypeptide, or a polypeptide fragment of said full-length Chp polypeptide, wherein (i) said Chp polypeptide or Chp polypeptide fragment has about 95% or greater identity to the amino acid sequence presented as SEQ ID NO:2, and (ii) said Chp polypeptide or Chp polypeptide fragment has at least one biological activity selected from the group consisting of a PAK regulatory domain binding activity, a PAK kinase stimulatory activity, a JNK kinase stimulatory activity, a cytoskeletal-reorganizing activity, a Chp-specific immunogenic activity directed to SEQ ID NO;2, and combinations thereof.

7. The isolated Chp polypeptide or polypeptide fragment of claim 1, wherein said Chp polypeptide or polypeptide fragment is obtained from a natural source.

8. The isolated Chp polypeptide or polypeptide fragment of claim 1, wherein said isolated Chp polypeptide fragment has about 95% or greater identity to an amino acid sequence selected from the group consisting of SEQ ID NO: 6, SEQ ID NO:7, SEQ ID NO:8, SEQ ID NO:9, SEQ ID NO:12, and SEQ ID NO:13.

9. An isolated full-length Chp polypeptide, wherein (i) said Chp polypeptide has about 95% or greater identity to the amino acid sequence presented as SEQ ID NO:2, and (ii) said Chp polypeptide has at least one biological activity selected from the group consisting of a PAK regulatory domain binding activity, a PAK kinase stimulatory activity, a JNK kinase stimulatory activity, a cytoskeletal-reorganizing activity, a Chp-specific immunogenic activity directed to SEQ ID NO:2, and combinations thereof.

10. The chimeric polypeptide of claim 6, wherein the Chp polypeptide comprises the amino acid sequence presented as SEQ ID NO:2.

11. The chimeric polypeptide of claim 6, wherein the Chp polypeptide fragment comprises at least one polypeptide having a sequence selected from the group consisting of SEQ ID NO: 6, SEQ ID NO:7, SEQ ID NO:8, SEQ ID NO:9, SEQ ID NO:12, and SEQ ID NO:13.

12. The chimeric polypeptide of claim 6, wherein the Chp polypeptide fragment is a Chp polypeptide fragment consisting essentially of a polypeptide having a sequence selected from the group consisting of SEQ ID NO: 6, SEQ ID NO:7, SEQ ID NO:8, SEQ ID NO:9, SEQ ID NO:12, and SEQ ID NO:13.

13. The chimeric polypeptide of claim 6, wherein the Chp polypeptide fragment has about 95% or greater identity to an amino acid sequence selected from the group consisting of SEQ ID NO: 6, SEQ ID NO:7, SEQ ID NO:8, SEQ ID NO:9, SEQ ID NO:12, and SEQ ID NO:13.

14. The chimeric polypeptide of claim 6, wherein said Chp polypeptide or Chp polypeptide fragment has about 98% or greater identity to the amino acid sequence presented as SEQ ID NO:2.

* * * * *

SEQUENCE LISTING

<160> NUMBER OF SEQ ID NOS: 5

<210> SEQ ID NO 1
<211> LENGTH: 1230
<212> TYPE: DNA
<213> ORGANISM: RAT Chp
<220> FEATURE:
<221> NAME/KEY: CDS
<222> LOCATION: (103)..(807)
<223> OTHER INFORMATION:

<400> SEQUENCE: 1

```
ggaattcggc acgagagatt gtcagcgtcc ggctgcggaa cctgcctccc tgagcgccgc      60
gagctggtcc gggctggccc ctctgctacc ccgggagcgg cc atg ccg ccg cgg       114
                                              Met Pro Pro Arg
                                                1 gag ctg agc gag gcc gag cca ccg cct ctc ccg gcc tcg acc cct cct      162
Glu Leu Ser Glu Ala Glu Pro Pro Leu Pro Ala Ser Thr Pro Pro
  5              10                  15                  20 ccg cgg cgg cgc agc gcc cct ccg gag ctg ggc atc aaa tgc gtg ctg      210
Pro Arg Arg Arg Ser Ala Pro Pro Glu Leu Gly Ile Lys Cys Val Leu
                 25                  30                  35 gtg ggc gat ggc gcg gtg ggc aag agc agc ctc atc gtc agc tac acc      258
Val Gly Asp Gly Ala Val Gly Lys Ser Ser Leu Ile Val Ser Tyr Thr
             40                  45                  50 tgc aat gga tac ccc tcg cgc tat cgg cct aca gca ctg gac act ttc      306
Cys Asn Gly Tyr Pro Ser Arg Tyr Arg Pro Thr Ala Leu Asp Thr Phe
         55                  60                  65 tcc gtg caa gtc ctg gta gat gga gcc cct gtg cga att gag ctc tgg      354
Ser Val Gln Val Leu Val Asp Gly Ala Pro Val Arg Ile Glu Leu Trp
     70                  75                  80 gac aca gca ggg cag gag gac ttt gac cgg ctt cgt tct ctc tgc tac      402
Asp Thr Ala Gly Gln Glu Asp Phe Asp Arg Leu Arg Ser Leu Cys Tyr
 85                  90                  95                 100 ccg gat acc gat gtc ttt ctg gct tgc ttc agc gtg gtg cag ccc agc      450
Pro Asp Thr Asp Val Phe Leu Ala Cys Phe Ser Val Val Gln Pro Ser
                105                 110                 115 tcc ttt caa aac ata aca gaa aaa tgg ctg ccg gag atc cgc act cac      498
Ser Phe Gln Asn Ile Thr Glu Lys Trp Leu Pro Glu Ile Arg Thr His
            120                 125                 130 aac ccc caa gca cct gtg ttg ctg gtg ggc act cag gcc gac ctg agg      546
Asn Pro Gln Ala Pro Val Leu Leu Val Gly Thr Gln Ala Asp Leu Arg
        135                 140                 145 gac gat gtc aat gta cta att cag ttg gac caa gga ggt cgg gag ggc      594
Asp Asp Val Asn Val Leu Ile Gln Leu Asp Gln Gly Gly Arg Glu Gly
    150                 155                 160 cca gta ccc gaa ccc caa gcc cag ggt ttg gct gag aag atc cgg gcc      642
Pro Val Pro Glu Pro Gln Ala Gln Gly Leu Ala Glu Lys Ile Arg Ala
165                 170                 175                 180 tgc tgc tac ctt gag tgc tca gcc ttg acg cag aag aac ttg aag gag      690
Cys Cys Tyr Leu Glu Cys Ser Ala Leu Thr Gln Lys Asn Leu Lys Glu
                185                 190                 195 gtg ttc gac tcg gcc att ctc agt gcg att gag cac aaa gcc cgc ctg      738
Val Phe Asp Ser Ala Ile Leu Ser Ala Ile Glu His Lys Ala Arg Leu
            200                 205                 210 gag aag aaa ctg aac gca aaa ggt gtg cgc acg ctc tct cgc tgt cgc      786
Glu Lys Lys Leu Asn Ala Lys Gly Val Arg Thr Leu Ser Arg Cys Arg
        215                 220                 225 tgg aag aag ttc ttc tgc ttt gtttgagcag ctatggcagt gcaagagata        837
Trp Lys Lys Phe Phe Cys Phe
```

```
Trp Lys Lys Phe Phe Cys Phe
        230                 235 ggcaggtggc ctgagacttc tggaccctga gacatcgggt actggcaggg cctggccaac    897
ccctgggact cagttctcta ttgaacacag gggatatggg cctcaaagct gtacactctg    957
gtaagccagg gtgtgcctct gtcctgtgca agggctggct gatttggatt tctttggtca   1017
agactcacag ggaaatccca gcactttggt tttcatggga tagttccatc agtgtcagta   1077
gcgctgagca gcttgtgatg taattctcag tttcttatcc tgggccacag gtcagtttgg   1137
ctgaatgcca ggtccctcgc tgggtcctca ccctctccta gcacaggtgt gacaaagcta   1197
ggaaaggaaa acagtgaggc atcctggagg gct                                1230
```

<210> SEQ ID NO 2
<211> LENGTH: 235
<212> TYPE: PRT
<213> ORGANISM: RAT Chp

<400> SEQUENCE: 2

```
Met Pro Pro Arg Glu Leu Ser Glu Ala Glu Pro Pro Leu Pro Ala
1               5                   10                  15

Ser Thr Pro Pro Arg Arg Arg Ser Ala Pro Pro Glu Leu Gly Ile
            20                  25                  30

Lys Cys Val Leu Val Gly Asp Gly Ala Val Gly Lys Ser Ser Leu Ile
            35                  40                  45

Val Ser Tyr Thr Cys Asn Gly Tyr Pro Ser Arg Tyr Arg Pro Thr Ala
50                  55                  60

Leu Asp Thr Phe Ser Val Gln Val Leu Val Asp Gly Ala Pro Val Arg
65                  70                  75                  80

Ile Glu Leu Trp Asp Thr Ala Gly Gln Glu Asp Phe Asp Arg Leu Arg
                85                  90                  95

Ser Leu Cys Tyr Pro Asp Thr Asp Val Phe Leu Ala Cys Phe Ser Val
                100                 105                 110

Val Gln Pro Ser Ser Phe Gln Asn Ile Thr Glu Lys Trp Leu Pro Glu
            115                 120                 125

Ile Arg Thr His Asn Pro Gln Ala Pro Val Leu Leu Val Gly Thr Gln
            130                 135                 140

Ala Asp Leu Arg Asp Asp Val Asn Val Leu Ile Gln Leu Asp Gln Gly
145                 150                 155                 160

Gly Arg Glu Gly Pro Val Pro Glu Pro Gln Ala Gln Gly Leu Ala Glu
                165                 170                 175

Lys Ile Arg Ala Cys Cys Tyr Leu Glu Cys Ser Ala Leu Thr Gln Lys
            180                 185                 190

Asn Leu Lys Glu Val Phe Asp Ser Ala Ile Leu Ser Ala Ile Glu His
            195                 200                 205

Lys Ala Arg Leu Glu Lys Lys Leu Asn Ala Lys Gly Val Arg Thr Leu
210                 215                 220

Ser Arg Cys Arg Trp Lys Lys Phe Phe Cys Phe
225                 230                 235
```

<210> SEQ ID NO 3
<211> LENGTH: 236
<212> TYPE: PRT
<213> ORGANISM: CHP

<400> SEQUENCE: 3

Met Pro Pro Arg Glu Leu Ser Glu Ala Glu Pro Pro Leu Pro Ala

```
                1               5                   10                  15

Ser Thr Pro Pro Pro Arg Arg Ser Ala Pro Pro Glu Leu Gly Ile
                20                  25                  30

Lys Cys Val Leu Val Gly Asp Gly Ala Val Gly Lys Ser Ser Leu Ile
        35                  40                  45

Val Ser Tyr Thr Cys Asn Gly Tyr Pro Ser Arg Tyr Arg Pro Thr Ala
    50                  55                  60

Leu Asp Thr Phe Ser Val Gln Val Leu Val Asp Gly Ala Pro Val Arg
65                  70                  75                  80

Ile Glu Leu Trp Asp Thr Ala Gly Gln Glu Asp Phe Asp Arg Leu Arg
                85                  90                  95

Ser Leu Cys Tyr Pro Asp Thr Asp Val Phe Leu Ala Cys Phe Ser Val
            100                 105                 110

Val Gln Pro Ser Ser Phe Gln Asn Ile Thr Glu Lys Trp Leu Pro Glu
        115                 120                 125

Ile Arg Thr His Asn Pro Gln Ala Pro Val Leu Leu Val Gly Thr Gln
    130                 135                 140

Ala Asp Leu Arg Asp Asp Val Asn Val Leu Ile Gln Leu Asp Gln Gly
145                 150                 155                 160

Gly Arg Glu Gly Pro Val Pro Glu Pro Gln Ala Gln Gly Leu Ala Glu
                165                 170                 175

Lys Ile Arg Ala Cys Cys Tyr Leu Glu Cys Ser Ala Leu Thr Gln Lys
            180                 185                 190

Asn Leu Lys Glu Val Phe Asp Ser Ala Ile Leu Ser Ala Ile Glu His
        195                 200                 205

Lys Ala Arg Leu Glu Lys Lys Leu Asn Ala Lys Gly Val Arg Thr Leu
    210                 215                 220

Ser Arg Cys Arg Trp Lys Lys Phe Phe Cys Phe Val
225                 230                 235

<210> SEQ ID NO 4
<211> LENGTH: 191
<212> TYPE: PRT
<213> ORGANISM: CDC42

<400> SEQUENCE: 4

Met Gln Thr Ile Lys Cys Val Val Val Gly Asp Gly Ala Val Gly Lys
1               5                   10                  15

Thr Cys Leu Leu Ile Ser Tyr Thr Thr Asn Lys Phe Pro Ser Glu Tyr
            20                  25                  30

Val Pro Thr Val Phe Asp Asn Tyr Ala Val Thr Val Met Ile Gly Gly
        35                  40                  45

Glu Pro Tyr Thr Leu Gly Leu Phe Asp Thr Ala Gly Gln Glu Asp Tyr
    50                  55                  60

Asp Arg Leu Arg Pro Leu Ser Tyr Pro Gln Thr Asp Val Phe Leu Val
65                  70                  75                  80

Cys Phe Ser Val Val Ser Pro Ser Ser Phe Glu Asn Val Lys Glu Lys
                85                  90                  95

Trp Val Pro Glu Ile Thr His His Cys Pro Lys Thr Pro Phe Leu Leu
            100                 105                 110

Val Gly Thr Gln Ile Asp Leu Arg Asp Asp Pro Ser Thr Ile Glu Lys
        115                 120                 125

Leu Ala Lys Asn Lys Gln Lys Pro Ile Thr Pro Glu Thr Ala Glu Lys
    130                 135                 140
```

-continued

```
Leu Ala Arg Asp Leu Lys Ala Val Lys Tyr Val Glu Cys Ser Ala Leu
145                 150                 155                 160

Thr Gln Lys Gly Leu Lys Asn Val Phe Asp Glu Ala Ile Leu Ala Ala
                165                 170                 175

Leu Glu Pro Pro Glu Pro Lys Lys Ser Arg Arg Cys Val Leu Leu
            180                 185                 190

<210> SEQ ID NO 5
<211> LENGTH: 192
<212> TYPE: PRT
<213> ORGANISM: RAC1

<400> SEQUENCE: 5

Met Gln Ala Ile Lys Cys Val Val Val Gly Asp Gly Ala Val Gly Lys
1               5                   10                  15

Thr Cys Leu Leu Ile Ser Tyr Thr Thr Asn Ala Phe Pro Gly Glu Tyr
                20                  25                  30

Ile Pro Thr Val Phe Asp Asn Tyr Ser Ala Asn Val Met Val Asp Gly
            35                  40                  45

Lys Pro Val Asn Leu Gly Leu Trp Asp Thr Ala Gly Gln Glu Asp Tyr
    50                  55                  60

Asp Arg Leu Arg Pro Leu Ser Tyr Pro Gln Thr Asp Val Phe Leu Ile
65                  70                  75                  80

Cys Phe Ser Leu Val Ser Pro Ala Ser Phe Glu Asn Val Arg Ala Lys
                85                  90                  95

Trp Tyr Pro Glu Val Arg His His Cys Pro Asn Thr Pro Ile Ile Leu
                100                 105                 110

Val Gly Thr Lys Leu Asp Leu Arg Asp Asp Lys Asp Thr Ile Glu Lys
            115                 120                 125

Leu Lys Glu Lys Lys Leu Thr Pro Ile Thr Tyr Pro Gln Gly Leu Ala
    130                 135                 140

Met Ala Lys Glu Ile Gly Ala Val Lys Tyr Leu Glu Cys Ser Ala Leu
145                 150                 155                 160

Thr Gln Arg Gly Leu Lys Thr Val Phe Asp Glu Ala Ile Arg Ala Val
                165                 170                 175

Leu Cys Pro Pro Pro Val Lys Lys Arg Lys Arg Lys Cys Leu Leu Leu
            180                 185                 190
```